US012582422B2

(12) United States Patent
Denham et al.

(10) Patent No.: US 12,582,422 B2
(45) Date of Patent: \*Mar. 24, 2026

(54) BONE ALIGN AND JOINT PREPARATION DEVICE AND METHOD

(71) Applicant: MEDARTIS AG, Basel (CH)

(72) Inventors: Greg Denham, Warsaw, IN (US); Ryan Schlotterback, Fort Wayne, IN (US); Daren Granger, Warsaw, IN (US)

(73) Assignee: MEDARTIS AG, Basel (CH)

( \* ) Notice: Subject to any disclaimer, the term of this patent is extended or adjusted under 35 U.S.C. 154(b) by 14 days.

This patent is subject to a terminal disclaimer.

(21) Appl. No.: 18/507,716

(22) Filed: Nov. 13, 2023

(65) Prior Publication Data

US 2024/0138857 A1 May 2, 2024

Related U.S. Application Data

(63) Continuation of application No. 17/652,195, filed on Feb. 23, 2022, now Pat. No. 11,826,062.

(51) Int. Cl.
*A61B 17/17* (2006.01)
*A61B 17/02* (2006.01)
(Continued)

(52) U.S. Cl.
CPC ........ *A61B 17/1775* (2016.11); *A61B 17/025* (2013.01); *A61B 17/151* (2013.01); *A61B 17/8061* (2013.01); *A61B 2017/565* (2013.01)

(58) Field of Classification Search
CPC ................................................. A61B 17/1775
See application file for complete search history.

(56) References Cited

U.S. PATENT DOCUMENTS

| | | | |
|---|---|---|---|
| 11,826,062 B2 * | 11/2023 | Denham | ............. A61B 17/025 |
| 2003/0097131 A1 * | 5/2003 | Schon | ............... A61B 17/7233 |
| | | | 606/62 |

(Continued)

FOREIGN PATENT DOCUMENTS

| | | |
|---|---|---|
| EP | 1508316 A1 | 2/2005 |
| GB | 2583572 A | 11/2020 |
| GB | 2589960 A | 6/2021 |

OTHER PUBLICATIONS

UKIPO Search Report dated Feb. 23, 2021.
(Continued)

*Primary Examiner* — Christian A Sevilla
(74) *Attorney, Agent, or Firm* — Heslin Rothenberg Farley and Mesiti P.C.; Victor A. Cardona, Esq.

(57) ABSTRACT

A bone displacement system includes an anchoring portion, a tool engaging portion, a compression distraction mechanism, a lateral body and a distal body. The anchoring portion has an aperture for receiving a wire to connect the anchoring portion to a proximal bone. The anchoring portion is connectable to a downwardly depending member for holding a tissue portion. The tool engaging portion is connected to the anchoring portion and is configured to connect a tool thereto. The compression-distraction mechanism is connected to the anchoring portion. The lateral body is connected to the compression-distraction mechanism and engageable with a lateral bone. The distal body is connected to the compression-distraction mechanism. The distal body has an aperture for receiving a wire to connect the distal body to a distal bone. The compression-distraction mechanism is configured to move the anchoring portion relative to the distal body.

16 Claims, 27 Drawing Sheets

(51) Int. Cl.
    *A61B 17/15*        (2006.01)
    *A61B 17/80*        (2006.01)
    *A61B 17/56*        (2006.01)

(56)              References Cited

U.S. PATENT DOCUMENTS

| | | | |
|---|---|---|---|
| 2016/0235414 A1* | 8/2016 | Hatch | A61B 17/1739 |
| 2017/0014143 A1* | 1/2017 | Dayton | A61B 17/15 |
| 2017/0020537 A1 | 1/2017 | Tuten | |
| 2017/0079669 A1 | 3/2017 | Bays et al. | |
| 2019/0274745 A1 | 9/2019 | Smith et al. | |
| 2021/0077131 A1 | 3/2021 | Denham et al. | |
| 2021/0330311 A1 | 10/2021 | Denham et al. | |
| 2021/0369287 A1 | 12/2021 | Boffeli et al. | |
| 2023/0077222 A1* | 3/2023 | Awtrey | A61B 17/1775 |

OTHER PUBLICATIONS

UKIPO Search Report dated Sep. 20, 2021.
UKIPO Combined Search and Examination Report dated Jul. 28, 2023, 2 pp.

\* cited by examiner

BONE ALIGN AND JOINT PREPARATION DEVICE AND METHOD

CROSS-REFERENCE TO RELATED APPLICATIONS

This application is a continuation of U.S. application Ser. No. 17/652,195 filed Feb. 23, 2022. The entire disclosure of the prior application is hereby incorporated herein by reference.

The present application relates to U.S. patent application Ser. No. 17/238,920 filed Apr. 23, 2021, which claims priority to U.S. Provisional Application Ser. No. 62/015,052 filed on Apr. 24, 2020, which are incorporated herein by reference in its entirety.

The present application is related to U.S. application Ser. No. 17/022,761 filed Sep. 16, 2020, which claims the benefit of U.S. Provisional Application Ser. No. 62/900,920 filed Sep. 16, 2019, U.S. Provisional Application No. 62/991,879 filed Mar. 19, 2020, and U.S. Provisional Application No. 63/015,052 filed Apr. 24, 2020, which are incorporated herein by reference in their entireties.

FIELD OF THE INVENTION

This application relates to apparatuses, devices, and methods for adjusting and joining bones.

DESCRIPTION OF THE RELATED ART

Hallux valgus is the medical term for a bunion. The first tarsal-metatarsal (TMT) joint is an important joint at the inner part of the middle of the foot. The two bones that meet to form this joint are the first metatarsal and medial cuneiform bones. When this joint has too much looseness or movement, the condition is known as hypermobility or instability. When this joint becomes hypermobile, the first metatarsal moves too much in one direction and the first toe compensates by moving too much in the other direction. When this happens, a bunion develops.

The bunion is a disease of the joint and soft tissue. A bunion deformity or hallux abducto valgus deformity results from the big toe deviating laterally toward the patient's smallest toe. Due to the lateral movement of the big toe, the first metatarsal bone angles toward the smaller toes on the patient's foot causing the first metatarsal bone to move out of alignment. Bunions may become irritating and, in some cases, very painful during walking and other weight bearing activities. Bunions may also be painful and debilitating condition that prevents wearing shoes. Genetics and poor shoe design are the causes. The angle between the metatarsal of the second digit is a means to quantify the degree of deformity.

Painful bunions are corrected by surgical soft tissue management and surgical bone reforming. The first metatarsal is corrected by sectioning it with a saw and moving the head laterally. There are numerous cut locations from the proximal to distal regions, namely the chevron, Ludloff, Mau and proximal. The bones are shifted, and held in place with screws, staples or plates. Sometimes adjacent joints are fused to stabilize the reconstruction.

The Lapidus procedure is a type of fusion of the first TMT joint that decreases the movement of that joint and straightens out the first metatarsal and toe, so the Lapidus procedure treats bunions caused by first TMT joint hypermobility.

The goal of the Lapidus procedure is to surgically treat hallux valgus that is caused by first TMT joint hypermobility. An orthopedic foot and ankle surgeon realigns to a normal toe shape by placing the first metatarsal straight with the medial cuneiform bone and locking or fusing these two bones together. When the first TMT joint is fused, the first metatarsal will not move abnormally. This will allow the first toe to stay straight and prevent the bunion from coming back.

Thus, a need exists for devices, systems, and methods for treating foot deformities that are repeatable yet adaptable to particular clinical situations.

SUMMARY OF THE INVENTION

The present invention provides, in a first aspect, a bone displacement system which includes an anchoring portion, a tool engaging portion, a compression distraction mechanism, a lateral body and a distal body. The anchoring portion has an aperture for receiving a wire to connect the anchoring portion to a proximal bone. The anchoring portion is connectable to a downwardly depending member for holding a tissue portion. The tool engaging portion is connected to the anchoring portion and is configured to connect a tool thereto. The compression-distraction mechanism is connected to the anchoring portion. The lateral body is connected to the compression-distraction mechanism and is engageable with a lateral bone. The distal body is connected to the compression-distraction mechanism. The distal body has an aperture for receiving a wire to connect the distal body to a distal bone. The compression-distraction mechanism is configured to move the anchoring portion relative to the distal body.

The present invention provides, in a second aspect, a method for use in bone displacement which includes inserting a first wire through an anchoring portion of a bone displacement mechanism into a first bone. A second wire is inserted through a distal body of the bone displacement mechanism distal to the anchoring portion into a second bone distal to the first bone. The distal body and the second bone are moved toward a lateral body of the bone displacement mechanism located laterally relative to the distal body and the anchoring portion to adjust an alignment of axes of the first bone and the second bone relative to each other. A downwardly depending member is connected to the anchoring portion for holding a tissue portion away from a joint between the first bone and the second bone.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the Drawings.

DETAILED DESCRIPTION OF THE EMBODIMENTS

Figure 1:
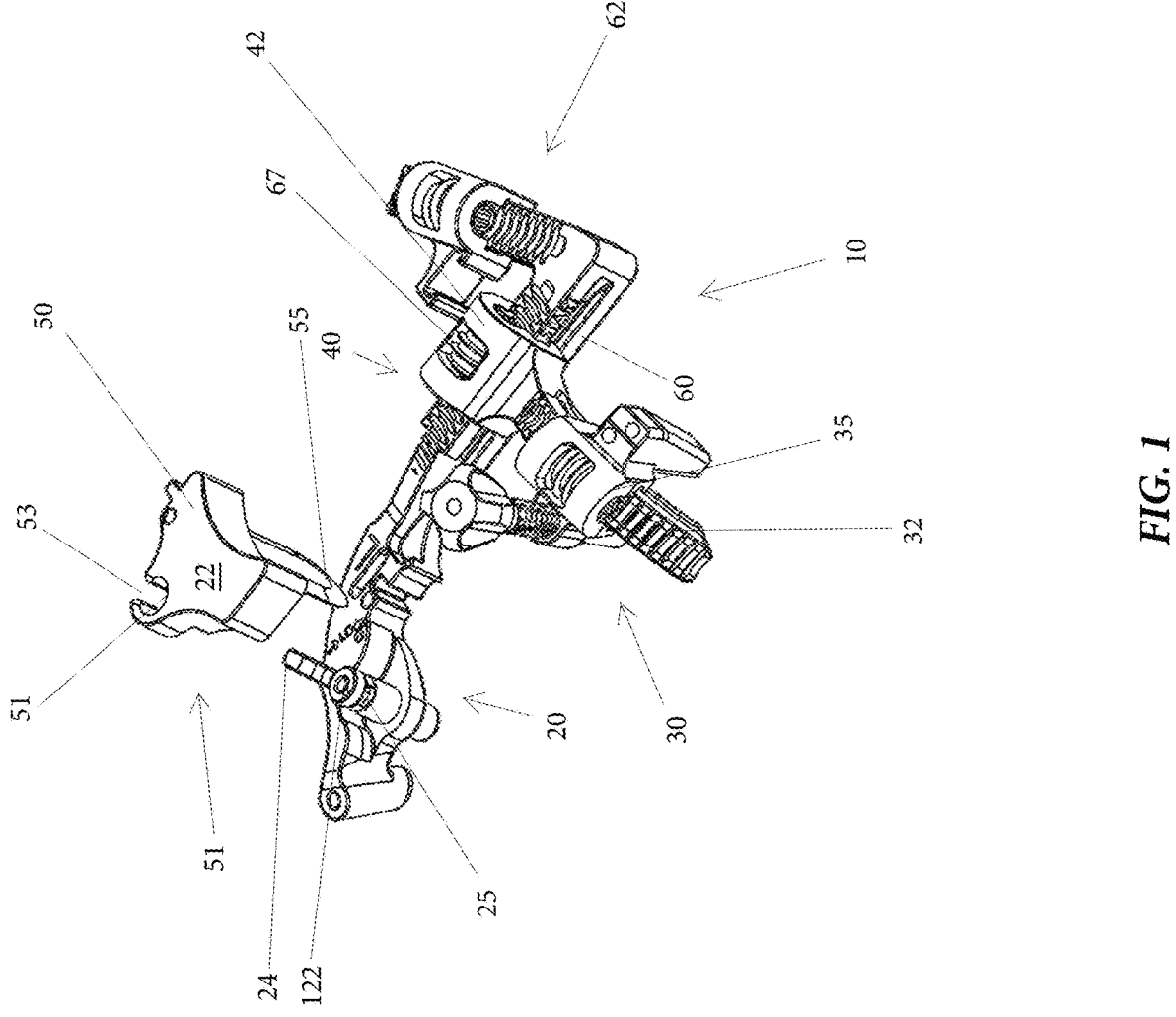
FIG. 1 is a perspective view of a bone displacement and cut guide system having a paddle cartridge shown separated therefrom.

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

The following description references systems, methods, and apparatuses for cutting tools for orthopedic surgery involving a foot or lower extremities. However, those possessing an ordinary level of skill in the relevant art will appreciate that other extremities, joints, and parts of the musculoskeletal system are suitable for use with the foregoing systems, methods and apparatuses. Likewise, the various figures, steps, procedures and work-flows are presented only as an example and in no way limit the systems, methods or apparatuses described to performing their respective tasks or outcomes in different time-frames or orders. The teachings of the present invention may be applied to any orthopedic surgery, such as on the hand as well as other upper and lower extremities and may be implemented in other treatments sites that have similar anatomical considerations.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As will be described below, the present invention includes systems and methods for correcting a deformity of the human foot. As depicted in FIGS. 1-26, a cut guide and bone displacement system 10 may include a cartridge engaging portion 20, a distal body, such as a pronation alignment trolley 30, an intermediate body, such as a compression-distraction mechanism 40, and a lateral member, such as a lateral extension mechanism 70. Cartridge engaging portion 20 may have an upwardly projecting portion 25 configured to engage a receiving portion of a tool, such as a paddle cartridge 50, for example.

Figure 5:
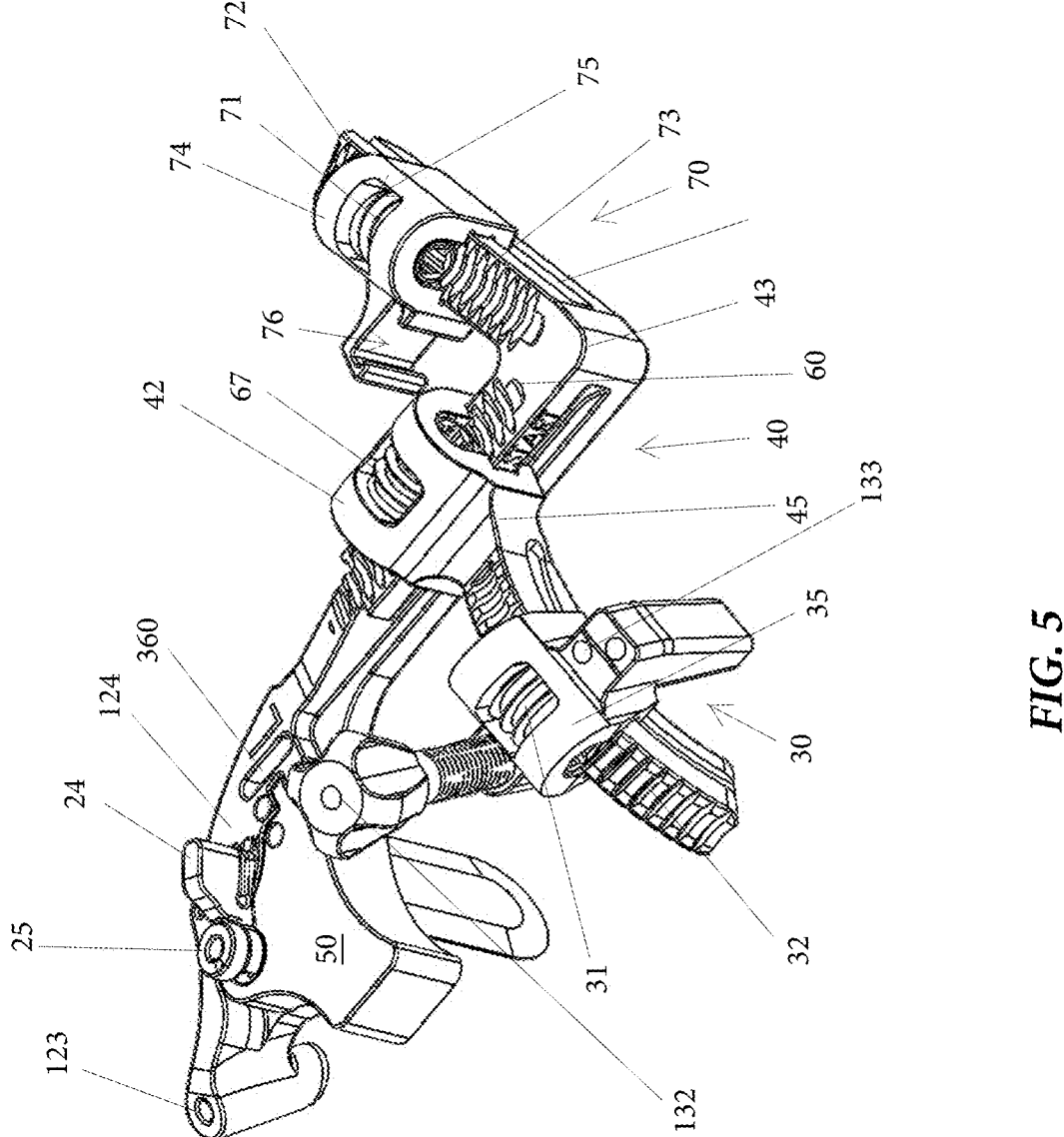
FIG. 5 is a top view of the system of FIG. 1 with the paddle cartridge locked to the cartridge engaging portion.
Figure 6:
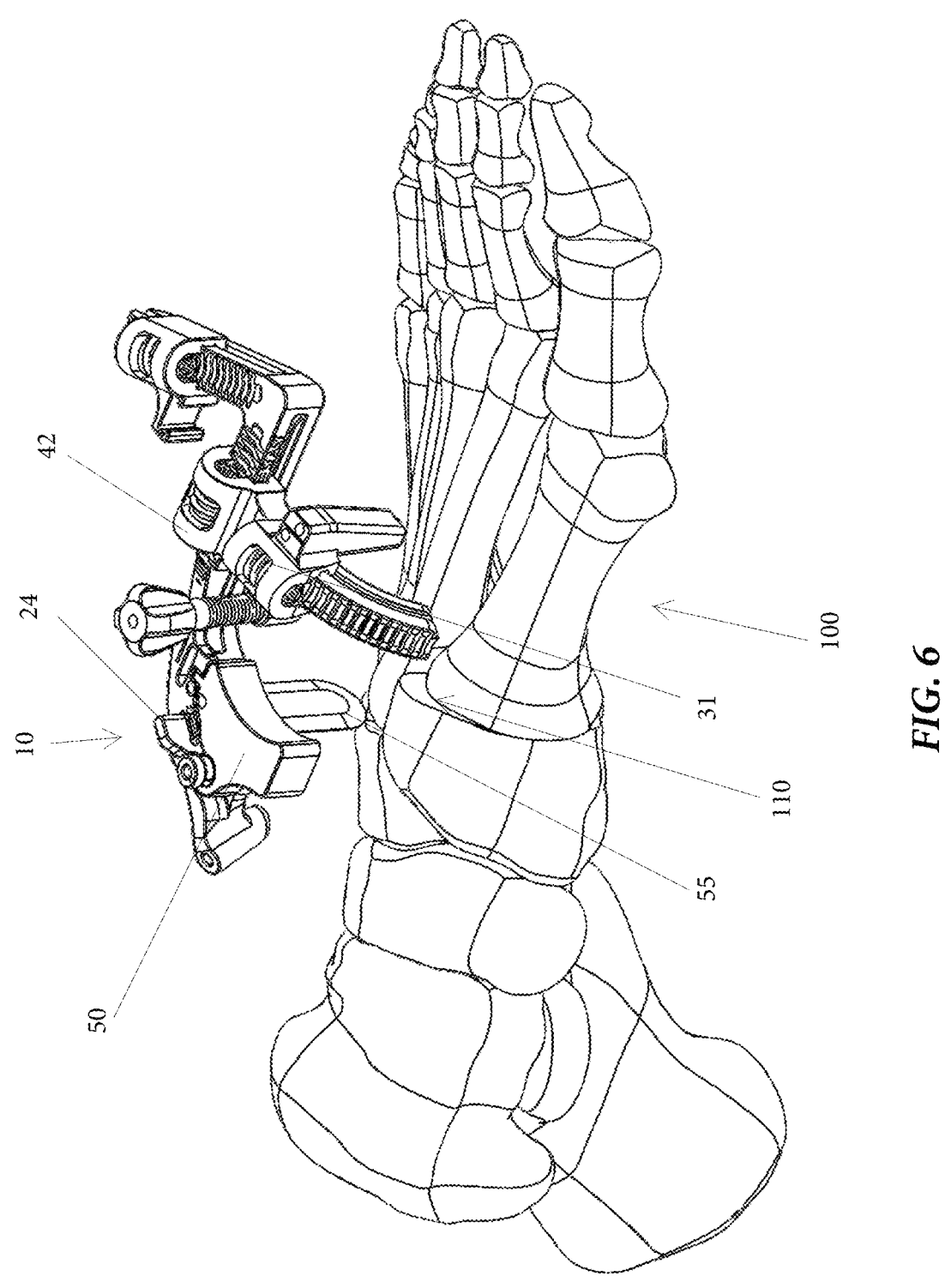
FIG. 6 is a perspective view of the system of FIG. 1 prior to engaging with a foot.
Figure 7:
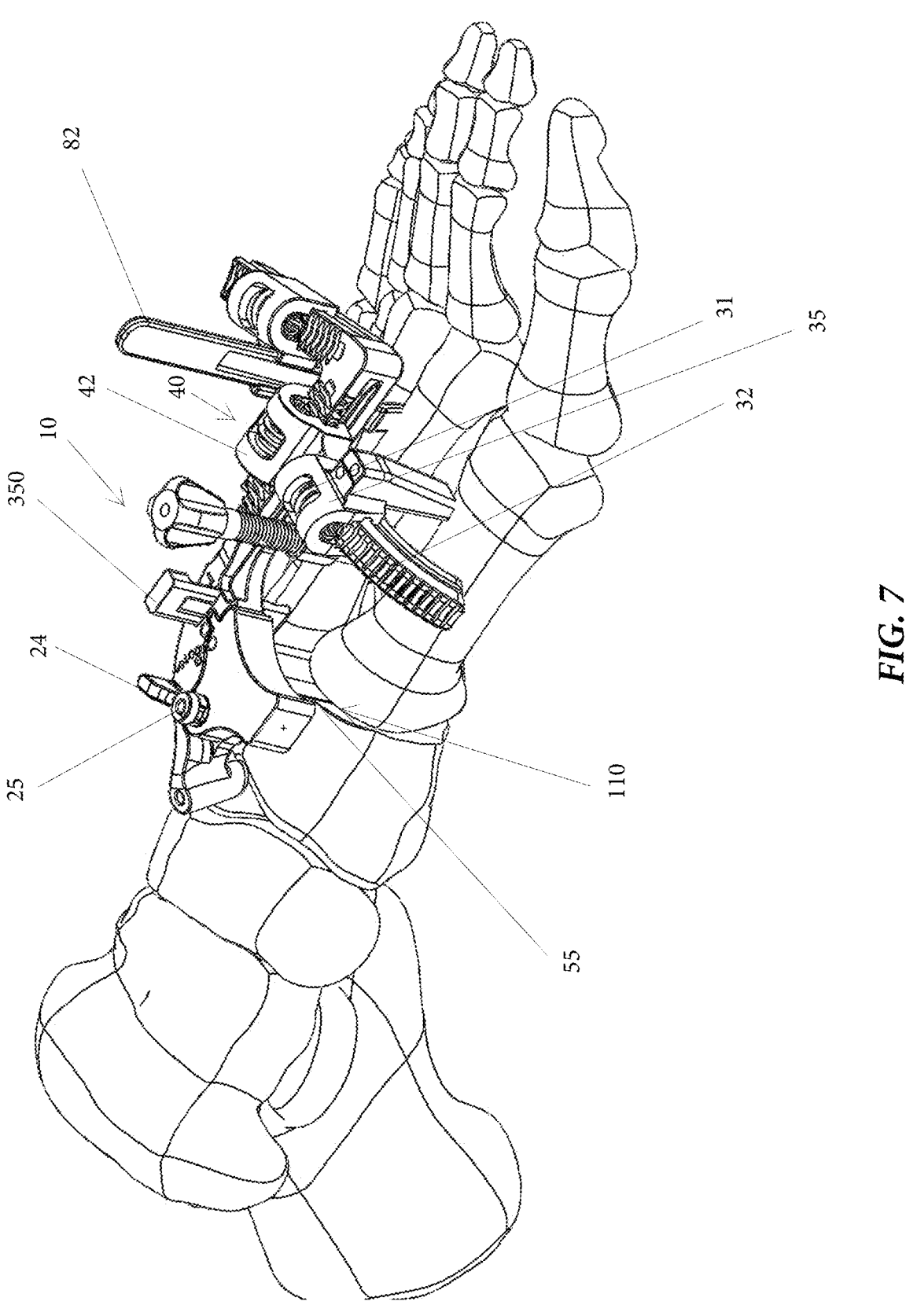
FIG. 7 is a perspective view of the system of FIG. 1 engaged with a foot with a paddle of the paddle cartridge received in a joint between a cuneiform and a metatarsal of the foot and a tissue paddle and lateral paddle engaged with the foot.
Figure 8:
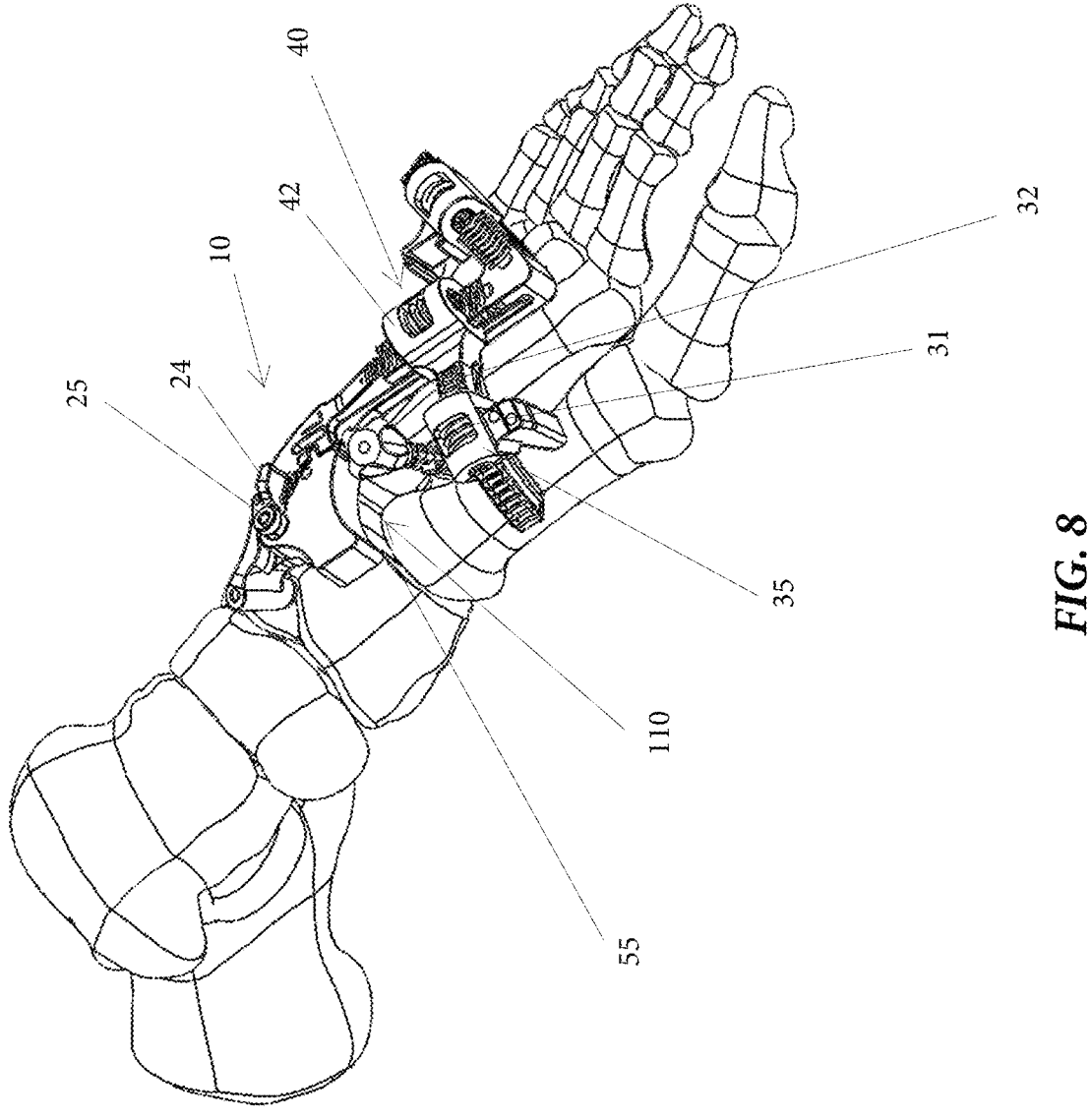
FIG. 8 is a perspective view of the system of FIG. 1 engaged with a foot with a paddle of the paddle cartridge received in a joint between a cuneiform and a metatarsal of the foot.

Alignment trolley 30 may include a mobile or holding portion 35 holding a worm screw 31 received within a recess 37 and movably engaged with teeth 33 to move along an axis of a threaded rail 32, as depicted for example in FIG. 5.

A connecting portion 45 may connect trolley 30 with compression-distraction mechanism 40. Compression-distraction mechanism 40 may include a mobile portion 42 engageable with an arm 60 connected to cartridge engaging portion 20. Mobile portion 42 may be movable along a longitudinal axis of arm 60. A worm screw 67 may move mobile portion 42 relative to arm 60, as described below, thereby moving alignment trolley 30, and lateral extension mechanism 70, as also described below, relative to arm 60. Arm 60 and rail 32 may have axes aligned perpendicular to each other, or approximately or about perpendicular.

Figure 2:
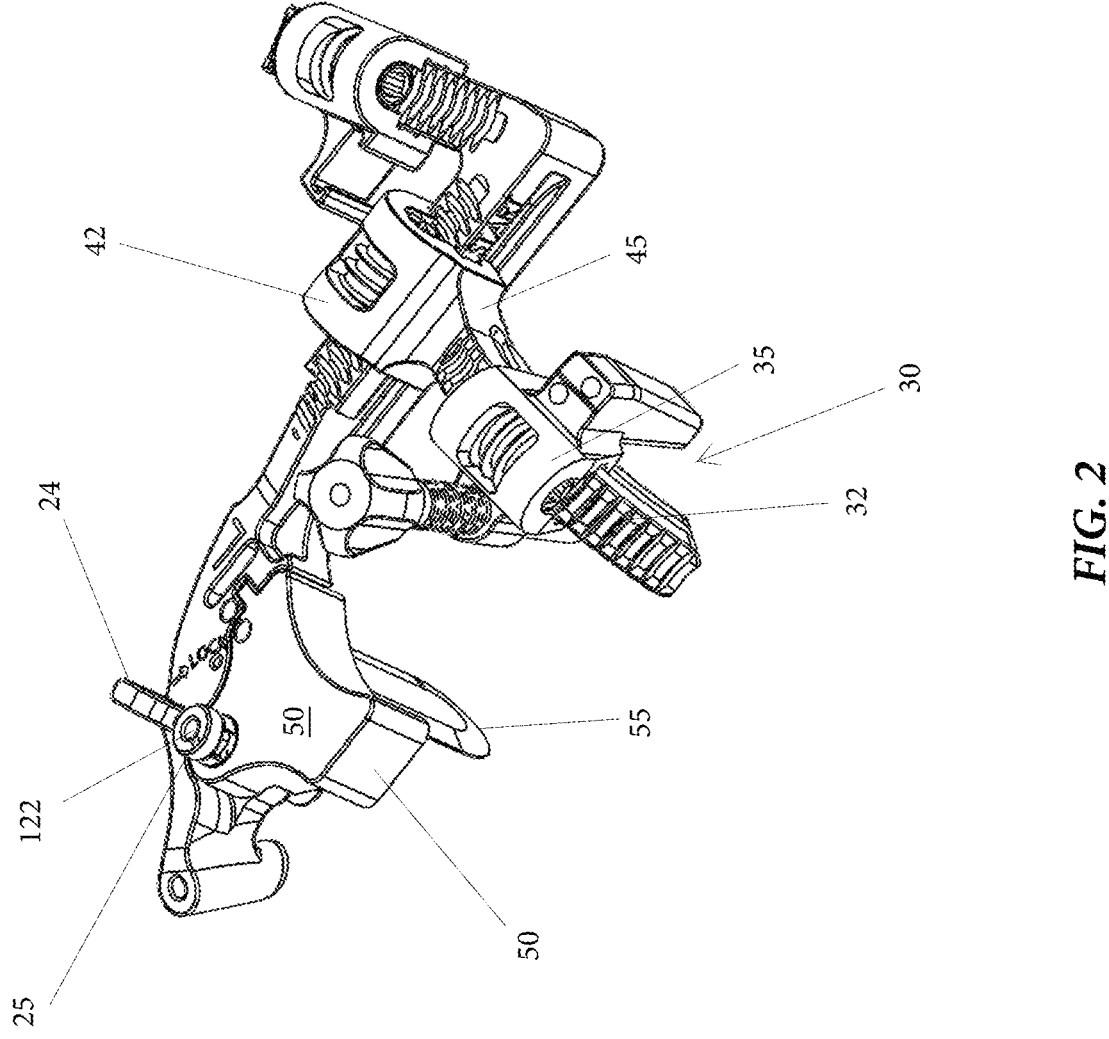
FIG. 2 is a perspective view of the system of FIG. 1 with the paddle cartridge connected to a cartridge engaging portion of the system.
Figure 3:
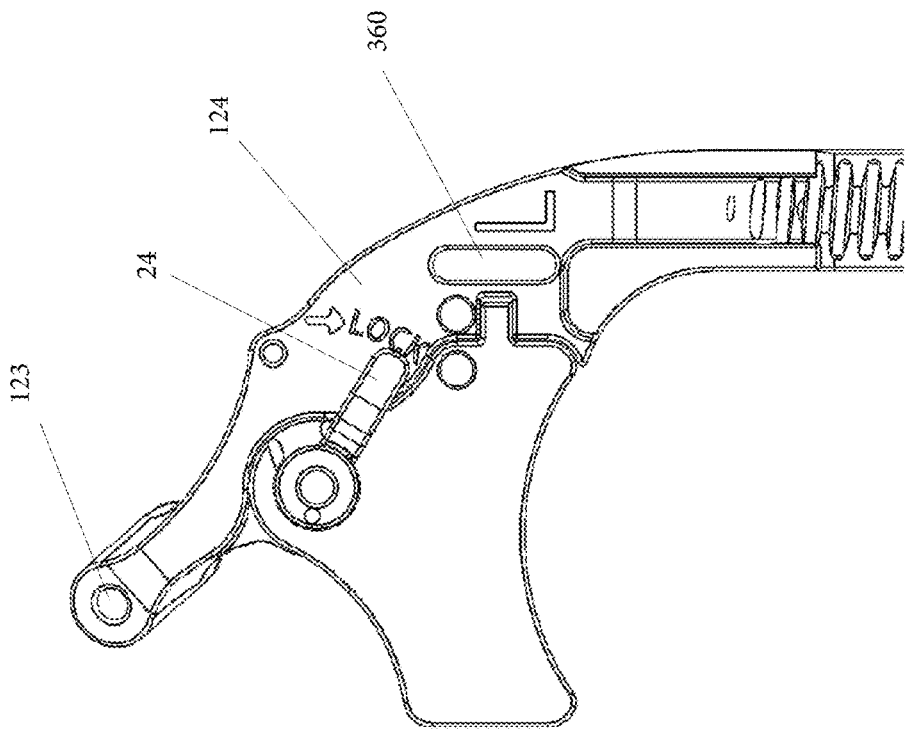
FIG. 3 is a top view of the cartridge engaging portion of the system of FIG. 1 with the paddle cartridge engaged thereto in a locked condition.
Figure 4:
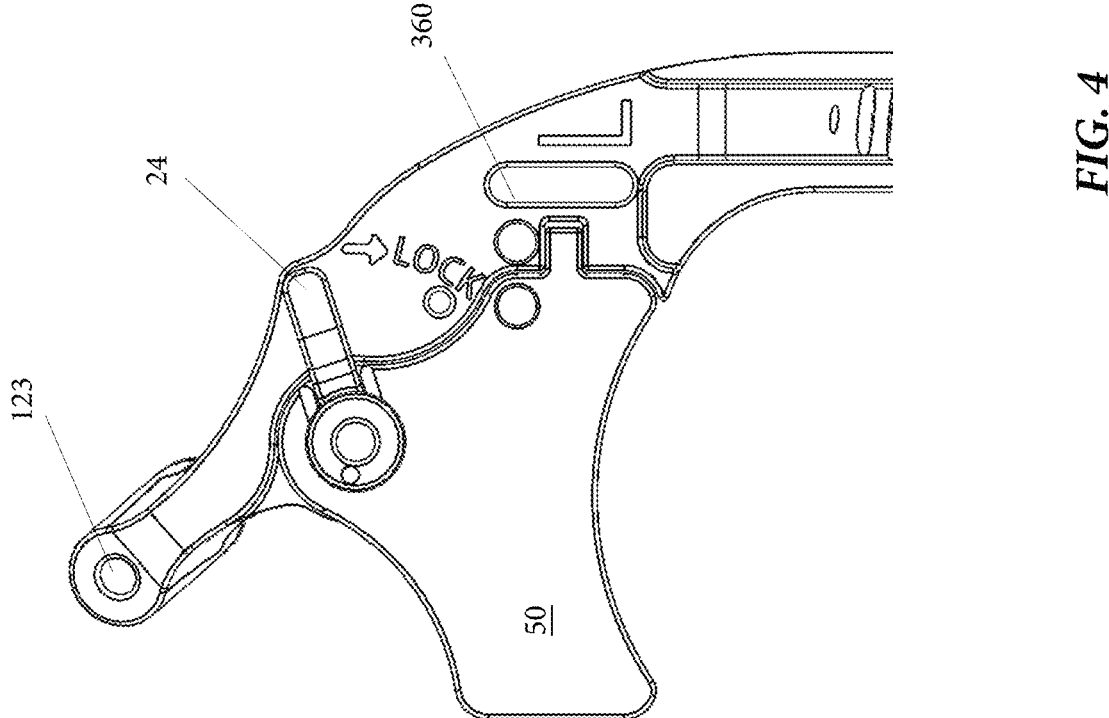
FIG. 4 is a top view of the cartridge engaging portion of the system of FIG. 1 with the paddle cartridge in an unlocked position relative to the cartridge engaging portion.

As depicted in FIGS. 1-2, a paddle cartridge 50 may include a receiving opening 51 and a slot 53 to receive a pin or upwardly projecting portion 25 and a handle 24, respectively, to releasably connect paddle cartridge 50 to cartridge engaging portion 20. Upwardly projecting portion 25 and handle 24 may be inserted through opening 51 and slot 53 such that handle 24 is above a top surface 22 of cartridge 50 and may be rotated such that handle 24 is located above and/or contacting top surface 22 to fix a cartridge (e.g., cartridge 50) into a connection with cartridge engaging portion 20. In particular, receiving opening 51 may be cylindrical for receiving upwardly projecting portion 25 which may also be cylindrical to allow a rotation of upwardly projecting portion 25 within receiving opening 51 to secure paddle cartridge 50 to cartridge engaging portion 20 as handle 24 is located above top surface 22 as depicted in FIG. 2 in an unlocked position. FIG. 3 depicts handle 24 after being inserted through receiving opening 51 but prior to such rotation, and FIGS. 4-5 depicts handle 24 in a rotated (locked) position.

Figure 9:
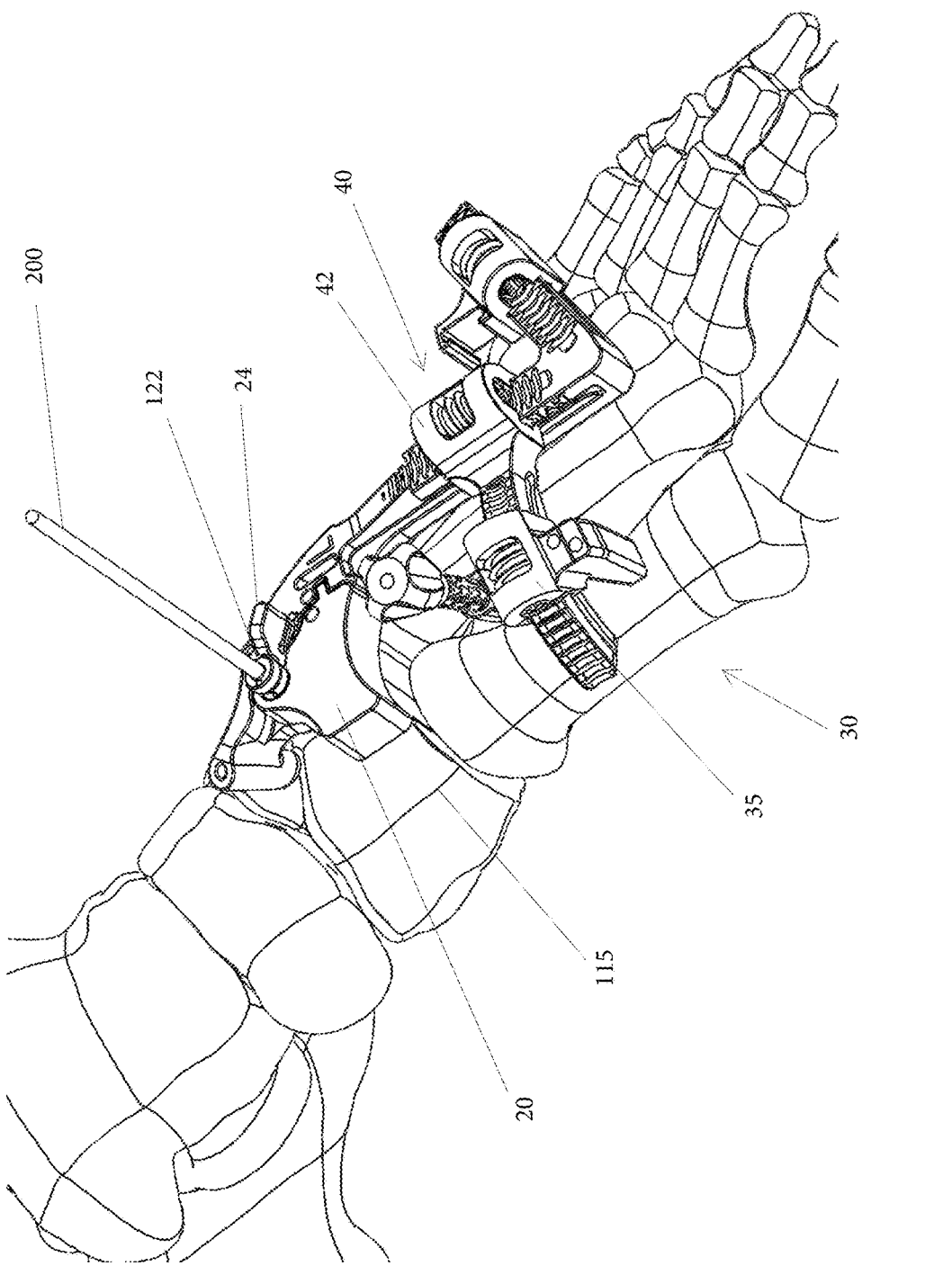
FIG. 9 is a perspective view of the system of FIG. 6 with a K-wire connecting the cartridge engaging portion with the cuneiform.

As depicted in FIGS. 6-9, system 10 may be engaged with a foot 100 by a downwardly depending joint arm or paddle 55 of paddle cartridge 50 being received in a first tarso-metatarsal joint space 110 to align system 10 relative to foot 100. A threaded pin or K-wire 200 may be inserted through a hole 122 in upwardly projecting portion 25 of cartridge engaging portion 20 received in receiving opening 51 into a proximal cuneiform 115 of foot 100 as depicted in FIG. 9.

Figure 10:
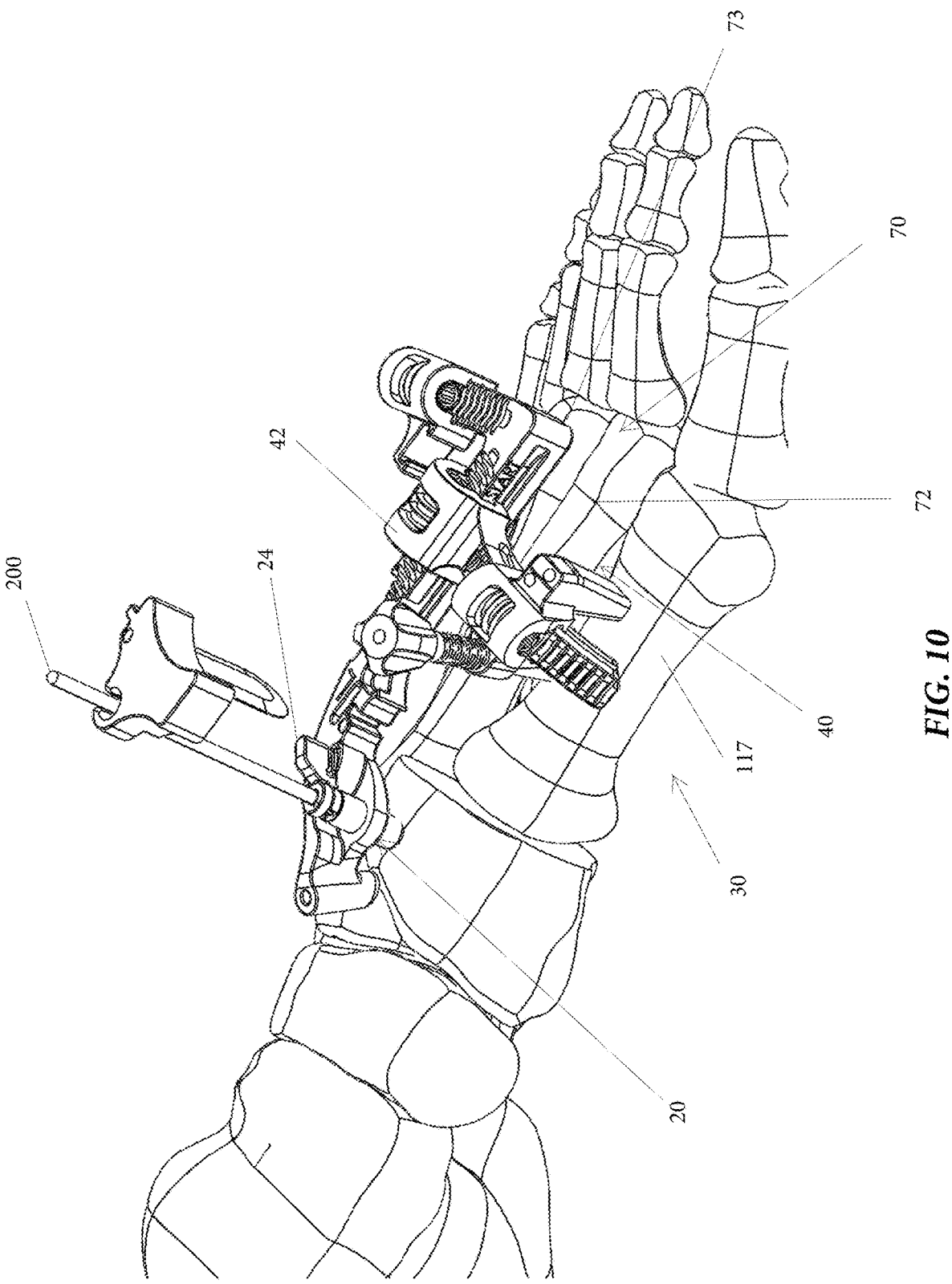
FIG. 10 is a perspective view of the system of FIG. 9 with the paddle cartridge being removed.

As depicted in FIG. 10 relative to FIG. 9, paddle cartridge 50 may then be removed from K-wire 200 after handle 24 and upwardly projecting portion 25 are rotated (e.g., counterclockwise) to allow handle 24 and upwardly projecting portion 25 to pass upwardly through receiving opening 51 and slot 53.

Figure 11:
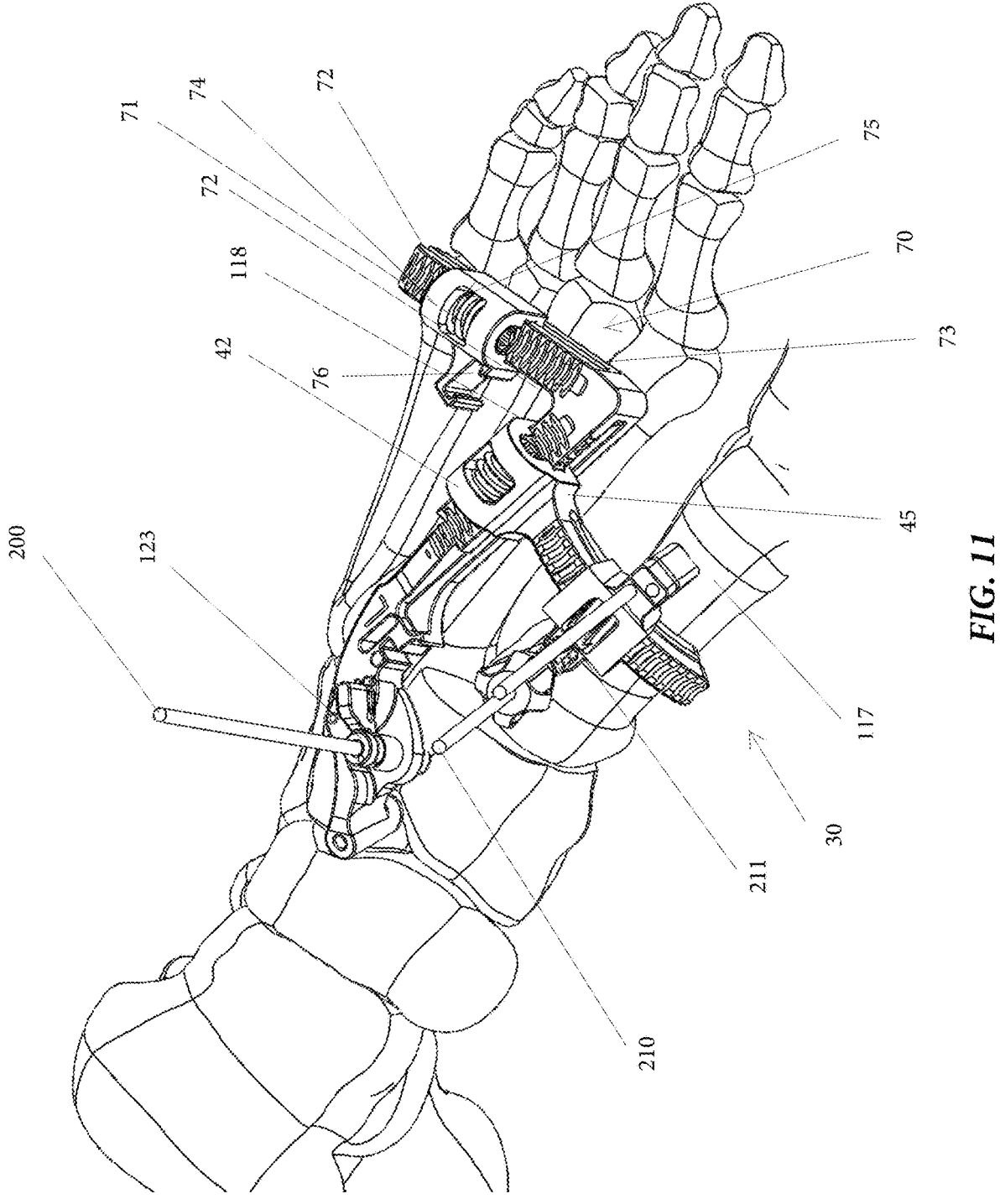
FIG. 11 a top view of the cartridge engaging portion of the system of FIG. 9 with K-wires connecting a holding portion of a trolley with the metatarsal.
Figure 12:
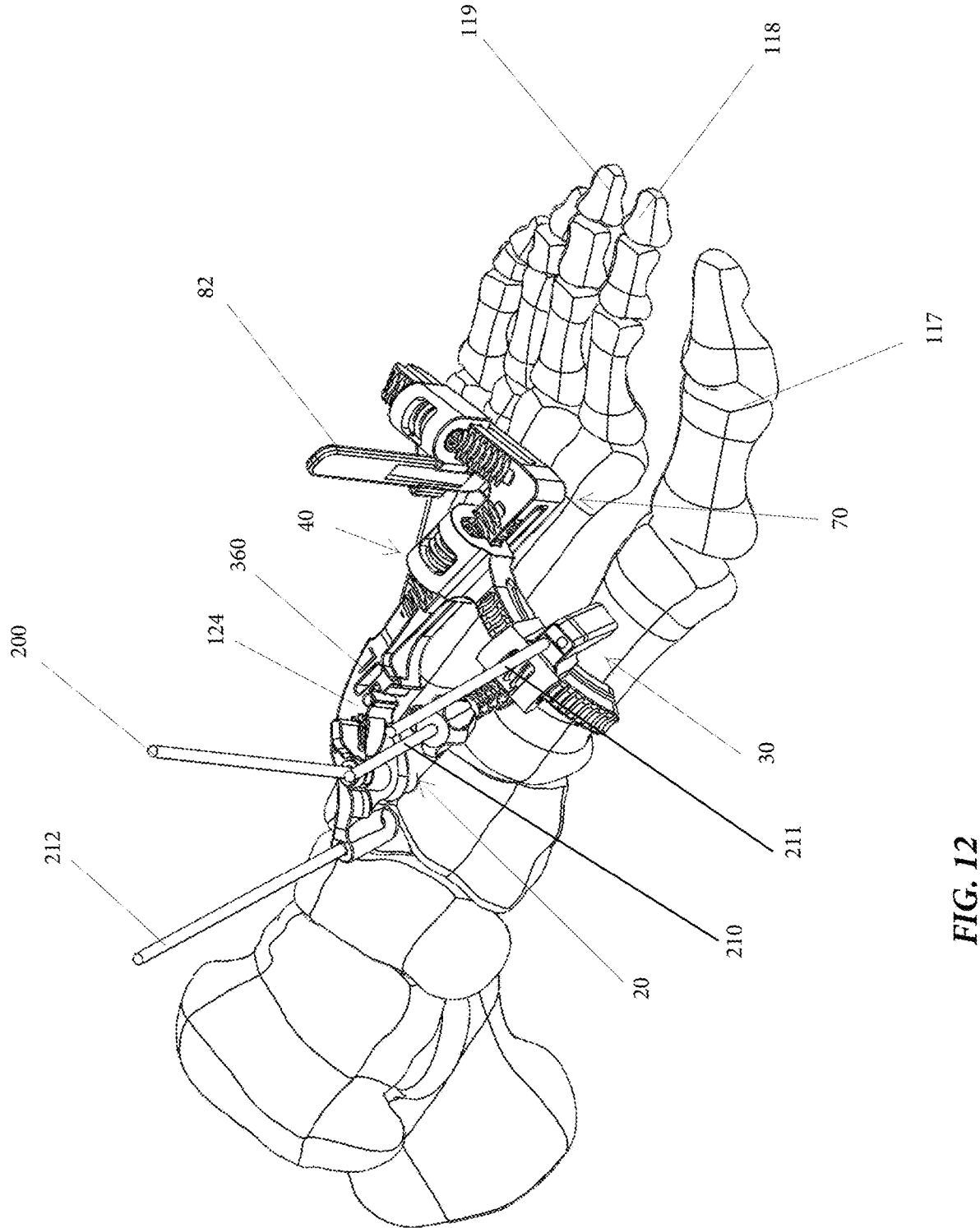
FIG. 12 is a perspective view of the system of FIG. 11 with a lateral paddle received in a lateral body and a K-wire received in an anchoring portion.

A second K-wire 210 may be inserted through a second opening 132 (FIG. 5) of holding portion 35 of trolley 30 and a third K-wire 211 may be inserted through a third opening 133 (FIG. 5) of holding portion 35 of trolley 30 to fix trolley 30 relative to a first metatarsal 117 as depicted in FIG. 11. Second opening 132 and third opening 133 may have parallel axes Lateral extension mechanism 70 may be connected to distraction mechanism 40 at a distal end 43 thereof. A paddle 82 may be received in a receiving cavity 76 (FIG. 11) of a lateral mobile or lateral holding portion 74 such that paddle 82 may extend through cavity 76 and may abut a side of a second metatarsal 118 as depicted in FIG. 12. Lateral mobile or lateral holding portion 74 may be located on an arm 72 of lateral extension mechanism 70 and may include a worm screw 71 received within a recess 75 and movably engaged with teeth 73 of arm 72 to move along an axis of arm 72.

Figure 26:
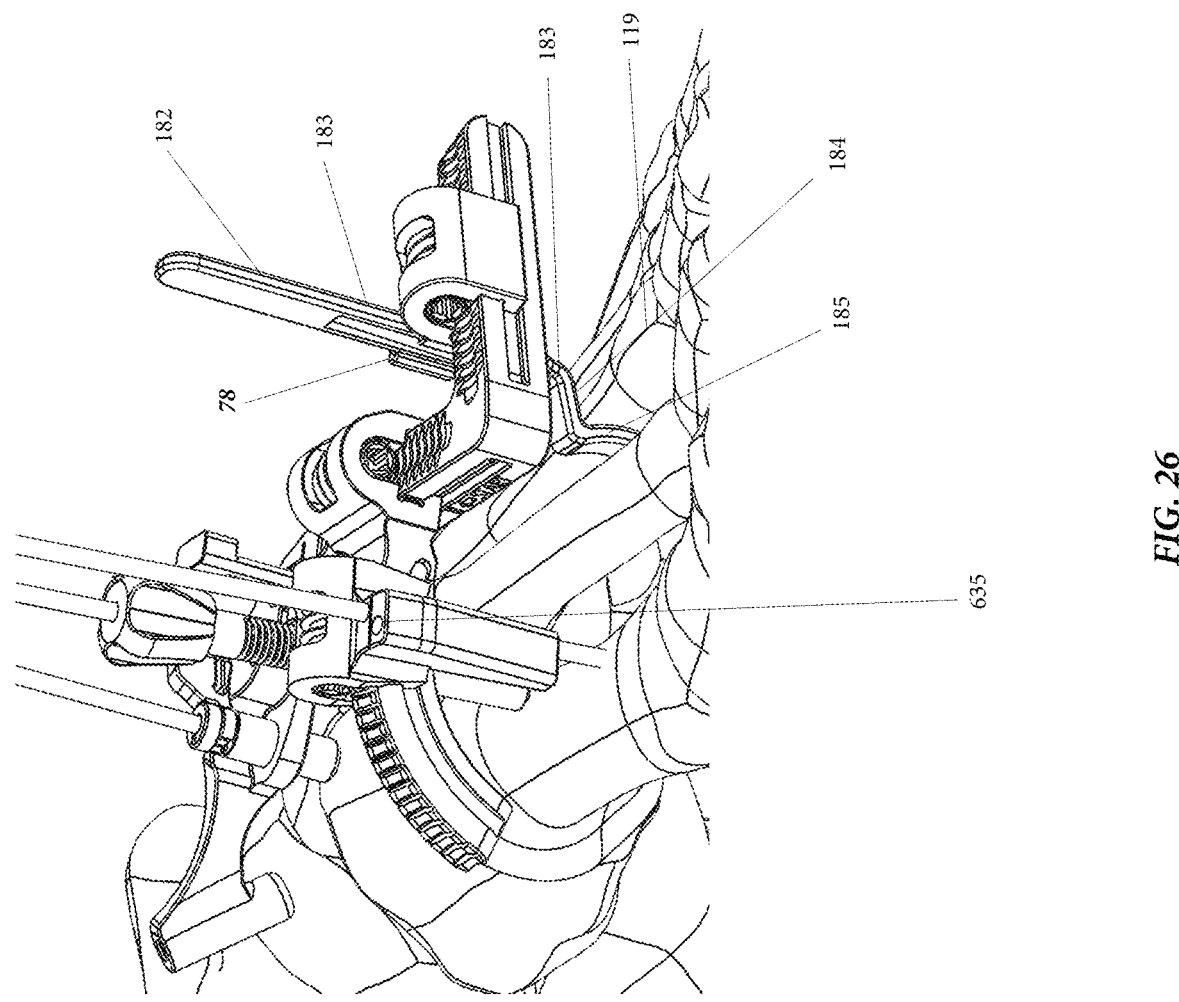
FIG. 26 is a front perspective view of the system of FIG. 25 after the plantar-dorsal adjustment mechanism provides the force to the metatarsal and a k-wire is inserted into the trolley to hold the metatarsal in the moved position.

In an example depicted in FIG. 26, a paddle 182 may be used in place of paddle 82 with paddle 182 having a linear portion 183 extending downwardly from cavity 76 bounded by receiving portion 78 of holding portion 74. A lateral portion 184 may be connected to linear portion 183 and a second linear portion 185 extending downwardly from lateral portion 184. Outside surfaces 186 of lateral portion 184 and second linear portion 185 may be curved or otherwise countoured to match third metatarsal 119 as depicted A valgus angle of first metatarsal 117 may be reduced by hand (e.g., by a surgeon) and/or by moving worm gear 71 of lateral extension member 70 to move alignment trolley 30 and compression-distraction mechanism 40 toward second metatarsal 118. For example, a user or surgeon may use a driver to engage a screw head 81 (FIG. 17) to cause a movement of worm screw 71 to move drive holding portion 74 to move along arm 72 as shown comparing FIG. 22 to FIG. 23. For example, such a movement of holding portion 74 may cause compression-distraction mechanism 40 to move over second metatarsal 118.

Figure 13:
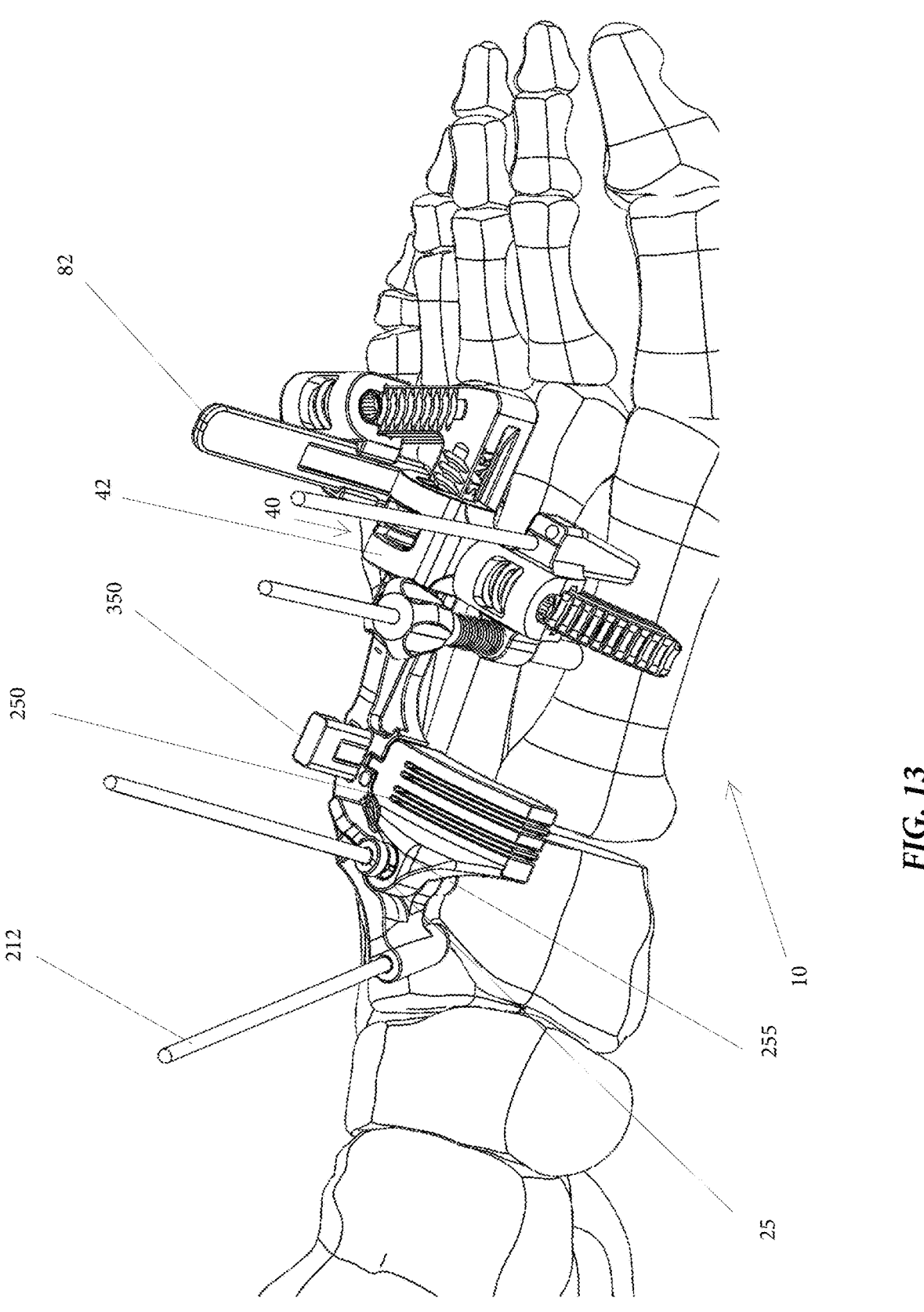
FIG. 13 is a perspective view of the system of FIG. 1 with a trolley holding portion rotated to correct a valgus angle of the first metatarsal and a cutting guide connected to a cartridge engaging portion.
Figure 14:
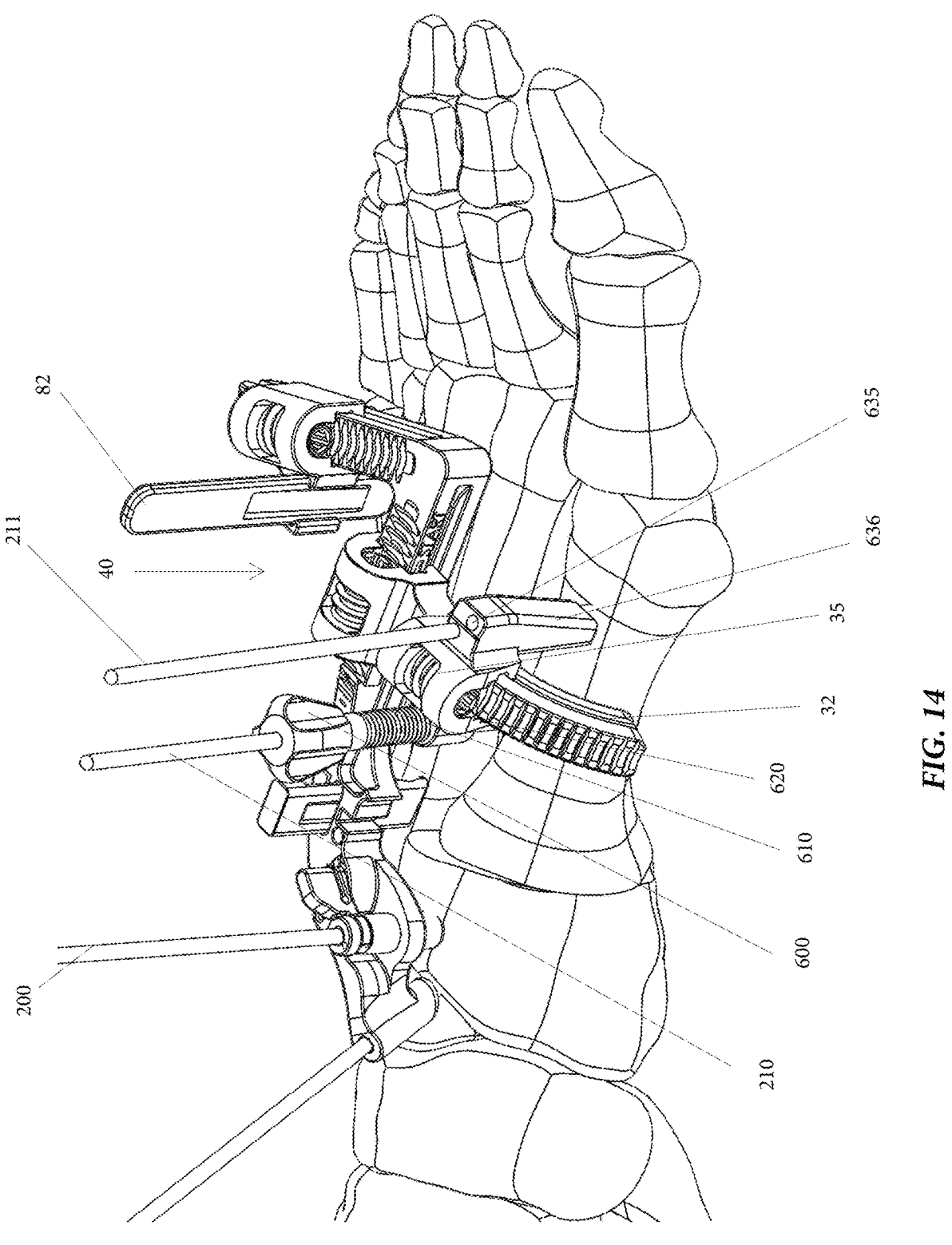
FIG. 14 is a perspective view of the system of FIG. 13 with a trolley holding with the cutting guide removed.

As depicted in FIGS. 11-14, holding portion 35 may be moved (e.g., via a manipulation or rotation of worm screw 31 by a user) along rail 32 of trolley 30 until a longitudinal dimension of K-wire 210 is perpendicular or about perpendicular to longitudinal dimensions of sesamoid grooves (not shown) of first metatarsal 117, as depicted in FIGS. 13-14. Such movement of holding portion 35 connected to first metatarsal 117 by second K-wire 210 and third K-wire 211 may further adjust the valgus angle of first metatarsal 117.

As depicted in FIGS. 11-12, a fourth K-wire 212 may be inserted through an anchoring hole 123 (FIG. 3) in a connecting or anchoring portion 124 between cartridge engaging portion 20 and distraction mechanism 40 to hold system 10 relative to foot 100 after holding portion 35 is moved on rails 32 and first metatarsal 117 is thus rotated, along with worm gear 71 being moved on rail 72 to an appropriate position as described above.

Figure 20:
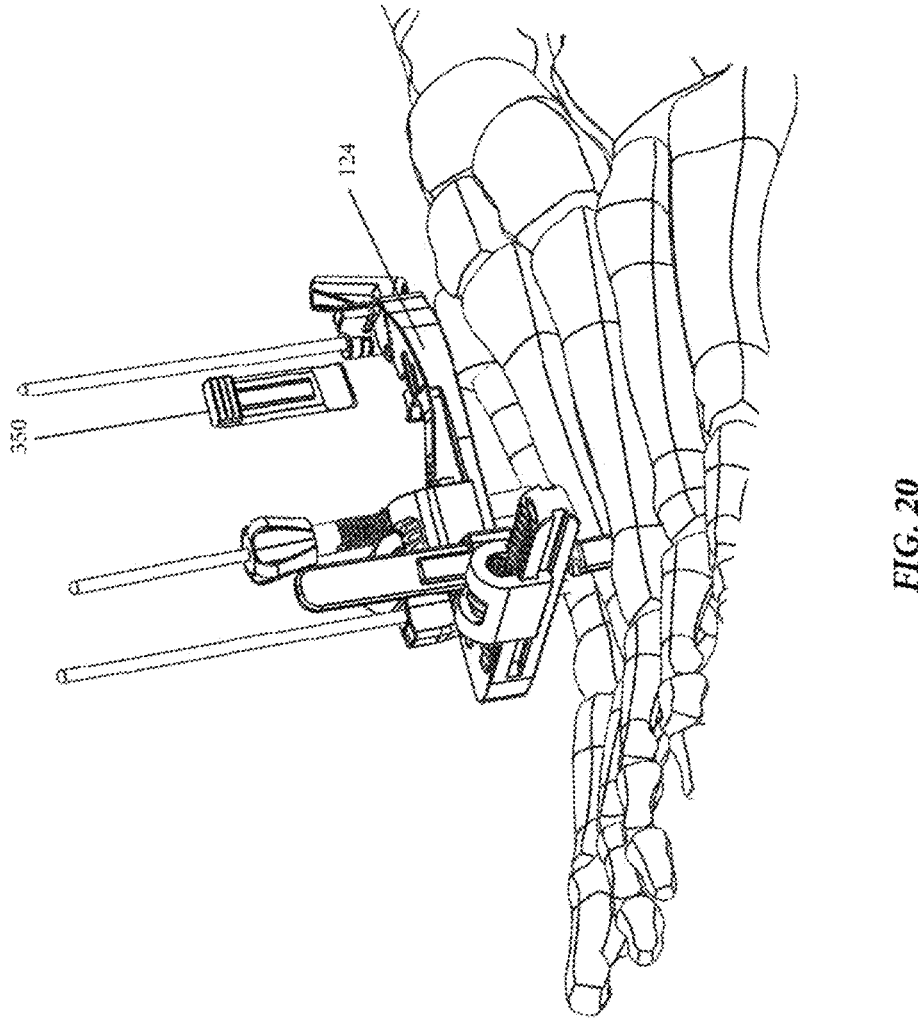
FIG. 20 is a perspective view of the system of FIG. 1 showing a tissue paddel prior to insertion in a receiving cavity of an anchoring portion.
Figure 21:
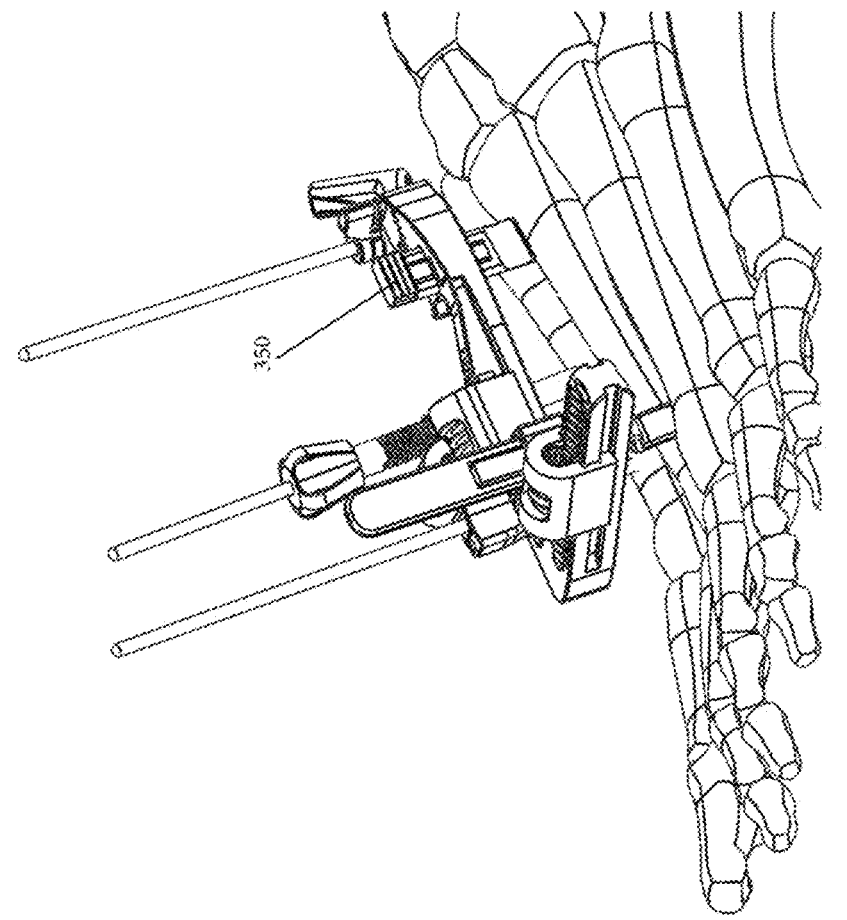
FIG. 21 is a side view of the system of FIG. 20 showing the tissue paddle being inserted in the anchoring portion.
Figure 22:
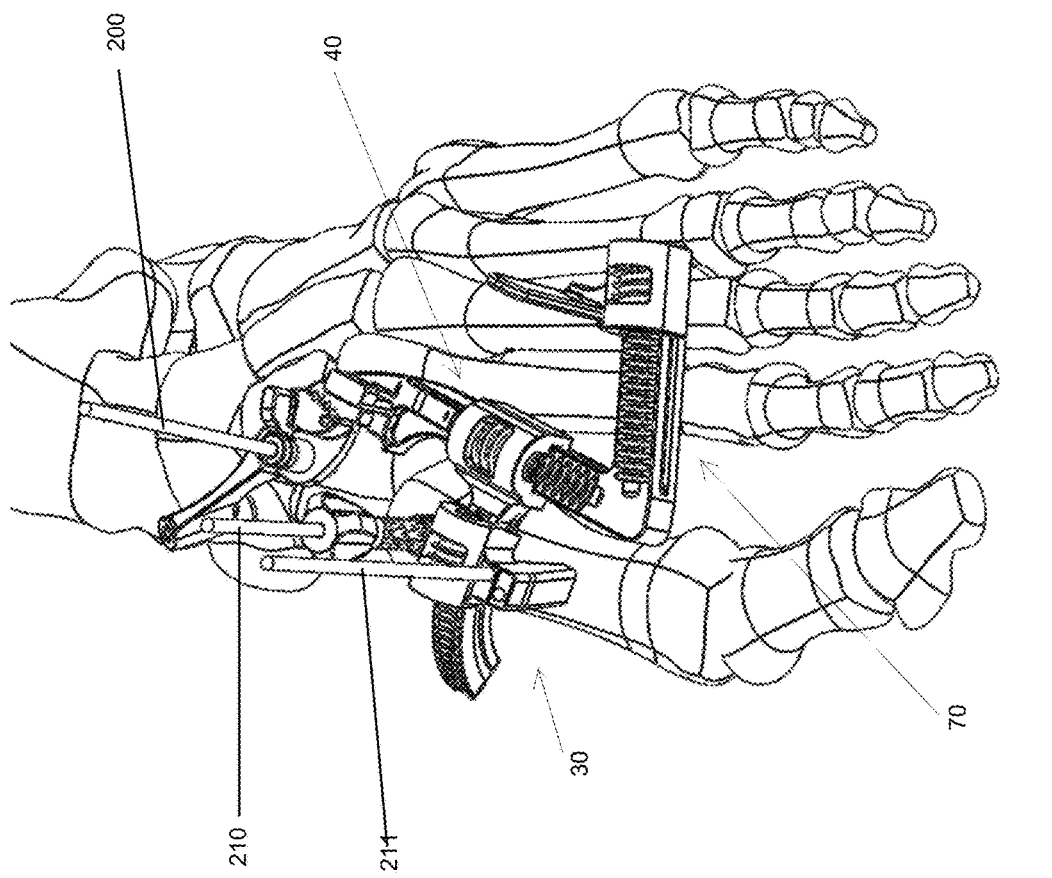
FIG. 22 is a perspective view of the system of FIG. 1 showing a movement of a holding portion along a rail of a lateral body to move a compression distraction mechanism relative to a lateral bone.
Figure 23:
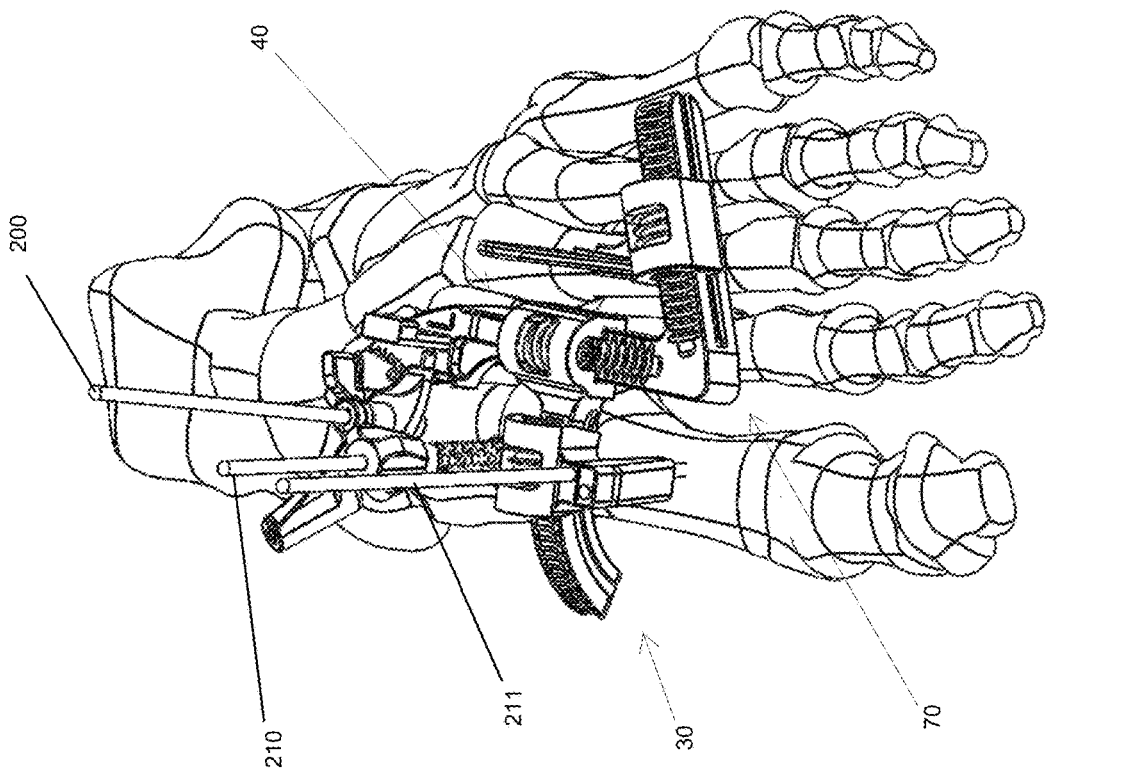
FIG. 23 is a perspective view of the system of FIG. 22 showing the holding portion at a different location on the rail relative to FIG. 22.

As depicted in FIGS. 13 and 20-21, a tissue paddle 350 may be received in a cavity or slot 360 of anchoring portion 124, such that paddle 350 may extend through cavity 360 and may hold tisssue below anchoring portion 124 in or near a location of bone to be cut. For example, when preparing a joint (e.g., first tarsometatarsal joint space 110) to allow a cutting of bones (e.g., proximal cuneiform 115 and/or first metatarsal 117), tissue paddle 350 may be inserted to hold tissue behind such paddle in a direction away from the joint (e.g., first tarsometatarsal joint space 110) to minimize interference between such tissue and and any instruments to engage the bones and/or joint space. In another example, tissue paddle 350 may be inserted in slot 360 prior to a reduction of a valgus angle of first metatarsal and/or a movement of or lateral holding portion 74 along arm 72, as described above, such that movement of system 10 may also move tissue behind tissue paddle 350 to a desired location.

Figure 28:
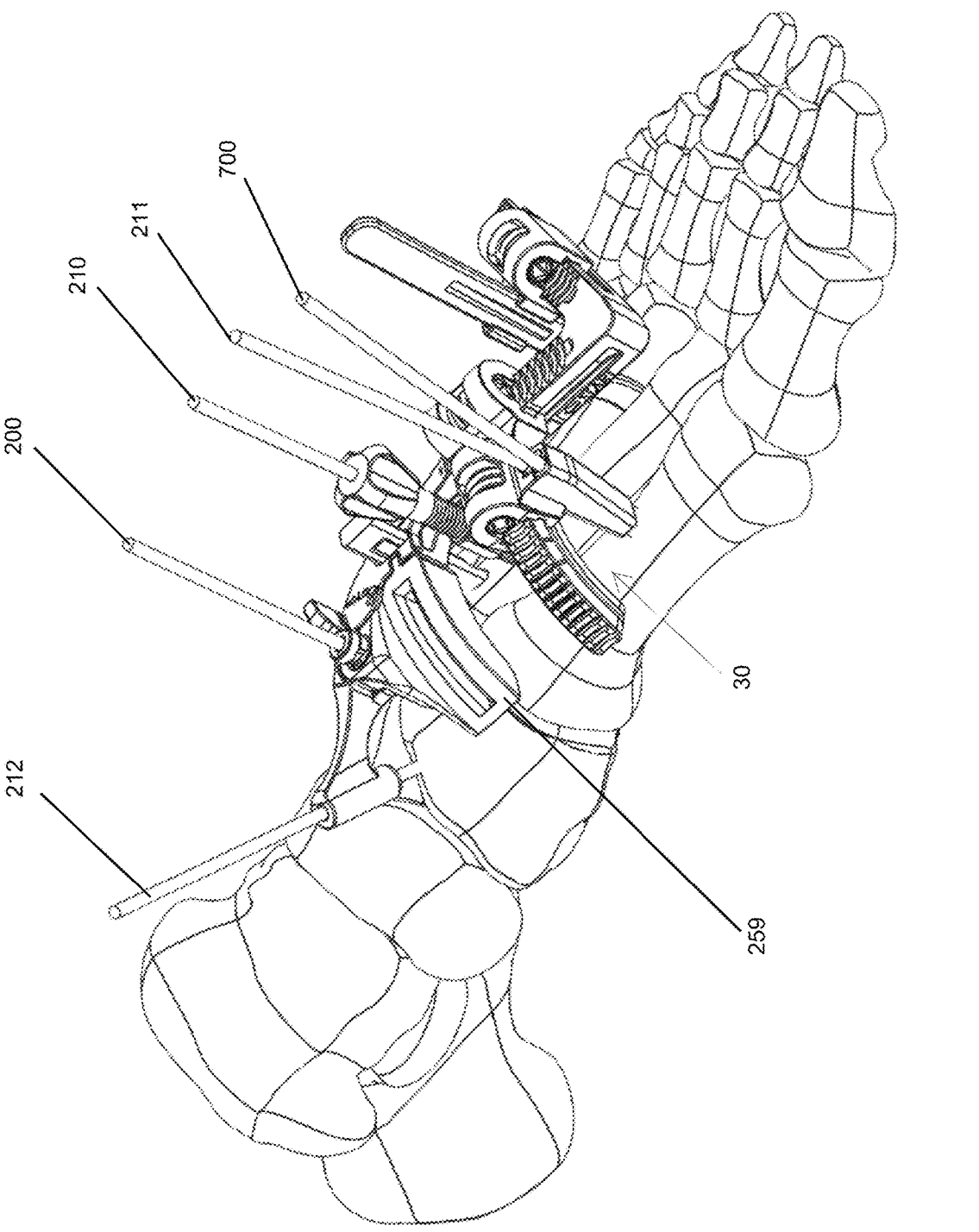
FIG. 28 is a perspective view of the system of FIG. 13 showing a Bur guide in place of the cutting guide.

As depicted in FIGS. 13-14, an open saw guide 250 may be attached to cartridge engaging portion 20 in a same manner as described above for attaching paddle cartridge 50 to cartridge engaging portion 20. Open saw guide 250 may have a recess 255 for receiving upwardly projecting portion 25 and handle 24 to allow such a connection. Similarly, a Bur guide cartridge 259 (FIG. 28)) may be attached to cartridge engaging portion 20 as described above for paddle cartridge 50. Such a Bur guide cartridge may have a recess (not shown) for receiving upwardly projecting portion 25 to allow such a connection. FIG. 14 depicts open saw guide 250 removed from cartridge engaging portion 20.

Open saw guide 250 may be utilized for an open procedure while Bur cartridge 259 may be used for a MIS (Minimally Invasive Surgery) procedure. Such an open procedure could involve an incision (e.g., of 4-5 cm) over a proximal metatarsal and medial cuneiform, for example, while an MIS procedure would involve incisions only at the locations necessary for the insertion of particular instruments (e.g., paddle 55). For example, a Bur guide cartridge (not shown) may include a 2.3 mm Shannon Bur usable to bur a joint space. In another example, if an open procedure is done (e.g., without the use of a cut guide) with Curettage or Microfracture then a cut guide cartridge would not be needed and thus not attached to cartridge engaging portion 20.

Figure 15:
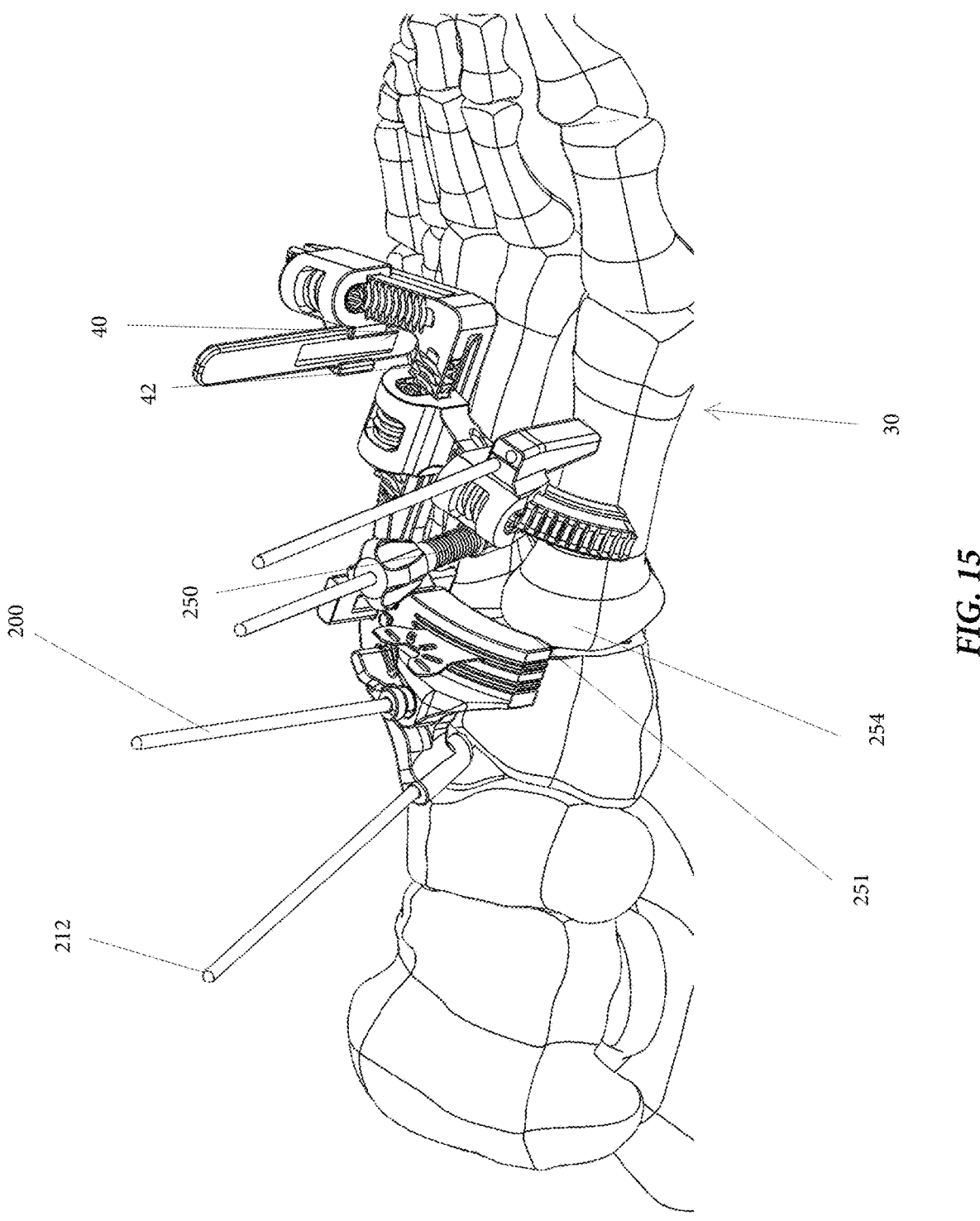
FIG. 15 is a perspective view of the system of FIG. 13 with a saw guide received in a saw slot of the open cut guide.
Figure 16:
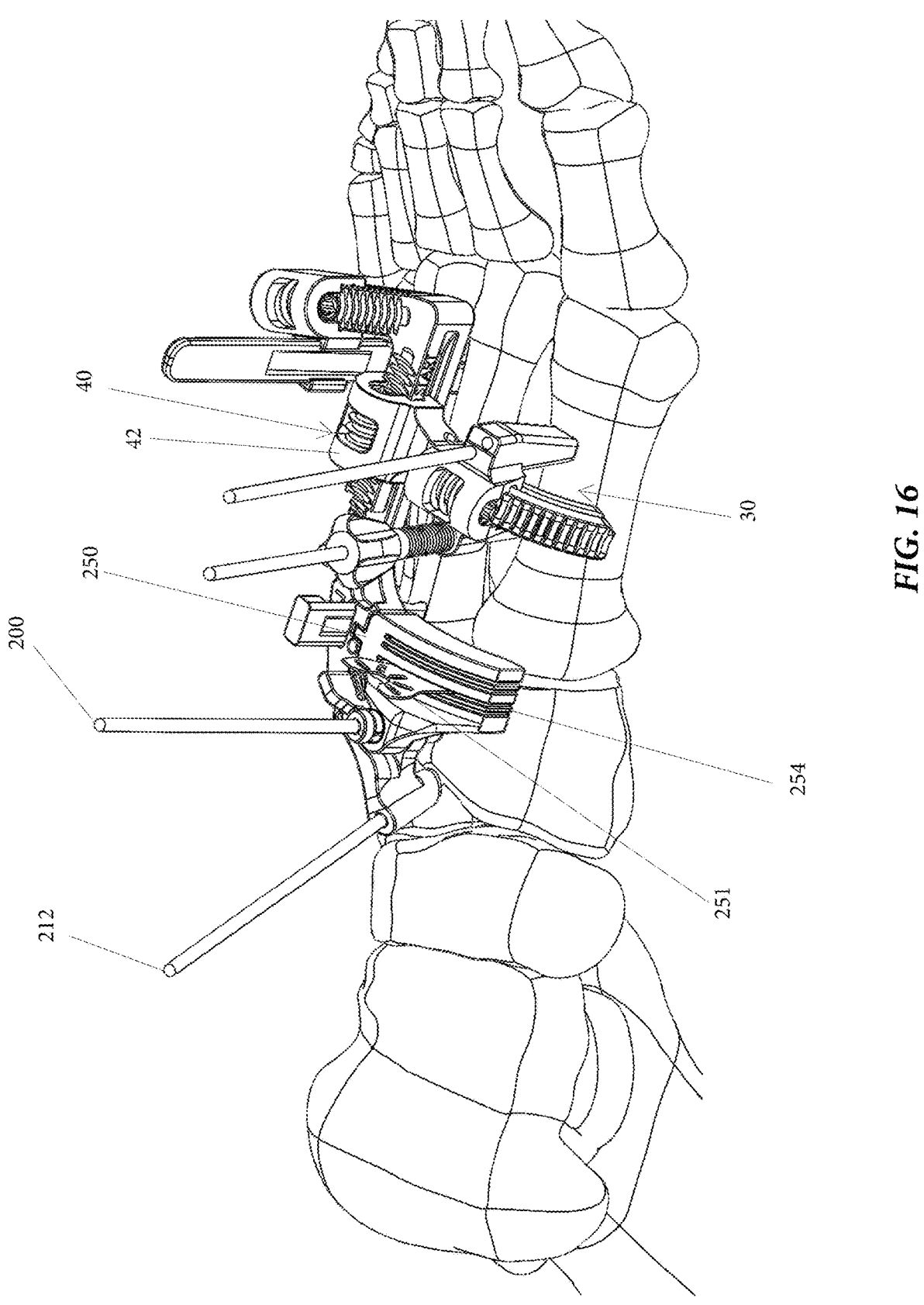
FIG. 16 is a perspective view of the system of FIG. 15 with the saw guide received in a different slot of the open saw guide relative to FIG. 15.

As depicted in FIG. 15, open saw guide 250 includes a first 1.5 mm cutting slot 252 and a first 3 mm cutting slot 253 to be utilized for cutting a cuneiform (e.g., proximal cuneiform 115) and a second 1.5 mm cutting slot 256 and a second 3 mm cutting slot 258 to be utilized for cutting a Metatarsal (e.g., first metatarsal 117), respectively, for example. FIG. 15 depicts such a cut of metatarsal 117 via slot 256 via slot 256 using a saw 251 and FIG. 16 depicts such a cut of proximal cuneiform 115 via slot 254.

Figures 24, 25:
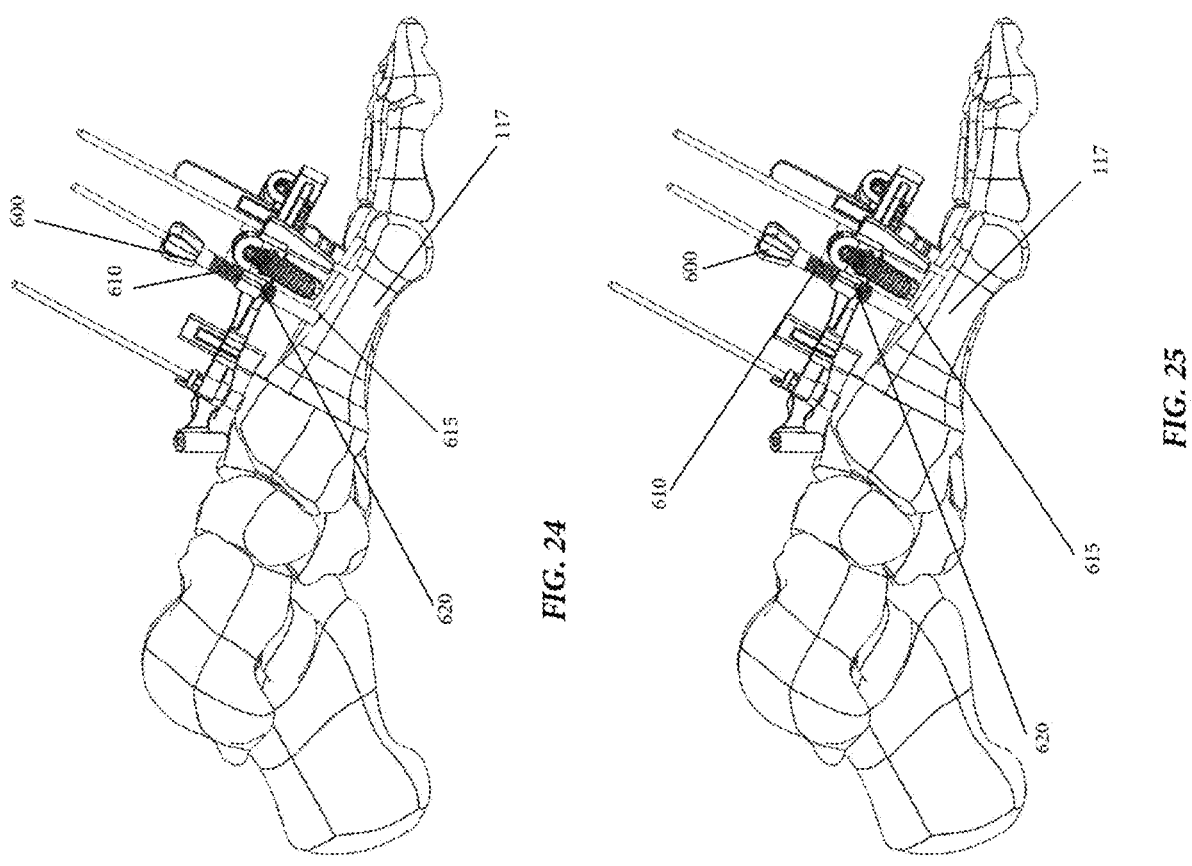
FIG. 24 is a perspective view of the system of FIG. 1 showing a plantar-dorsal adjustment mechanism connected to a trolley in a first position relative to a metatarsal below the trolley.
FIG. 25 is a perspective view of the system of FIG. 24 showing the plantar-dorsal adjustment mechanism connected to the trolley in a second position relative to the metatarsal below the trolley after the plantar-dorsal adjustment mechanism provides a force to the metatarsal.

As depicted in FIGS. 14 and 24-25, for example, a plantar-dorsal adjustment mechanism 601 may include a drive handle 600 connected to a threaded member 610 which is threadingly engaged to a threaded receiver 620 connected to holding portion 35. K-wire 210 may be received in second opening 132 of holding portion 35 of trolley 30. A bottom end 615 of threaded member 610 may extend below a threaded receiver 620 and may contact a bone (e.g., first metatarsal 117) below trolley 30. Handle 600 may be rotated by a user or surgeon to raise or lower bottom end 615 of threaded member 610. For example, a user may rotate handle 600 to cause a lowering of bottom end 615 to cause the end to contact and move the bone (e.g., metararsal 117) downwardly (e.g., a plantar shift), such as after the cutting of a metatarsal (e.g., metararsal 117) and/or cuneiform (e.g., cuneiform 115) as described above. The described movement due to a force applied by end 615 on the metatarsal may place an axis of the metatarsal in a desired alignment.

Figure 27:
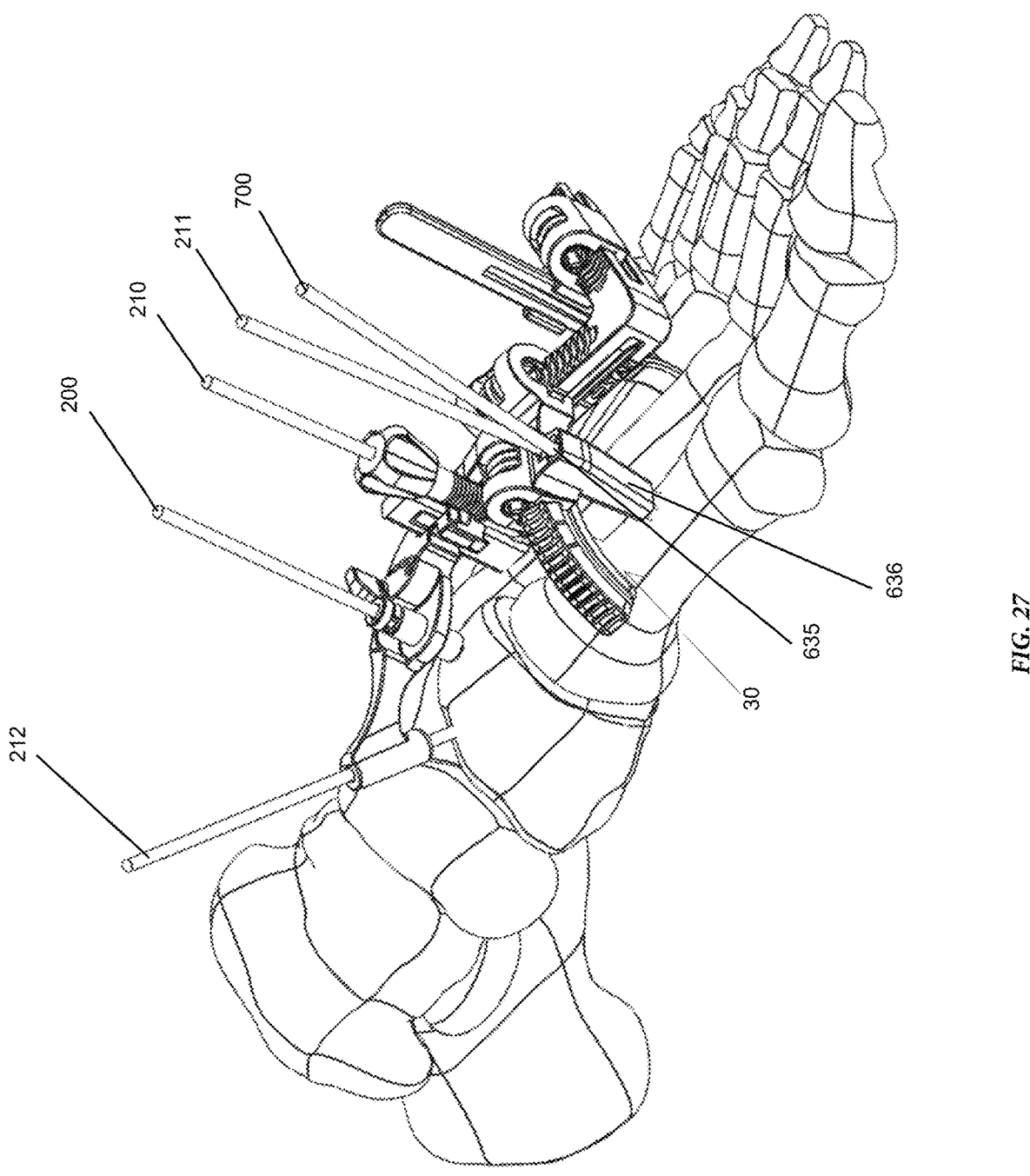
FIG. 27 is a perspective view of the system of FIG. 25 after the plantar-dorsal adjustment mechanism provides the force to the metatarsal and a k-wire is inserted into the trolley to hold the metatarsal in the moved position.

After such an adjustment of a metatarsal (e.g., metararsal 117) by an adjustment mechanism (e.g., a plantar-dorsal adjustment mechanism 601) a fifth K-wire 700 may be inserted through a third opening 635 of a downwardly depending portion 636 of holding portion 35 of trolley 30 to hold the metatarsal in the moved position as depicted in FIG. 27. For example, fifth K-wire 700 may be aligned at a non-parallel angle relative to the other K-wires (e.g., K-wires 210, 211) connected to holding portion 35 of trolley 30 and the metarsal such that fifth K-wire 700 may hold the metarsal in such a plantar-dorsal position, for example. Downwardly depending portion 636 may receive align K-wire 211 and fifth K-wire 700 to maintain alignment and avoid bending of the K-wires without contacting the metatarsal (e.g., metararsal 117) which the K-wires connect to. Further, such plantar-dorsal adjustment may occur before or after a removal of cartiliage as described below.

In operation, no portion of any surface of holding portion 35 of trolley 30 through which the K-wires (e.g., K-wire 210, K-wire 211) extend towards the first metatarsal (e.g., first metatarsal 117) may touch the first metatarsal. For example, downwardly depending portion 636 avoids contact with the first metatarsal (e.g., first metatarsal 117). Further, other portions (e.g., rail 32) of alignment trolley may avoid contact with the first metatarsal (e.g., first metatarsal 117). Such spacing by the trolley above the bone may inhibit or prevent alingment trolley 30 from causing a mis-alignment of system 10, e.g., prevent the trolley from acting like a pry bar to lift a cuneiform attachment (e.g., a K-wire) of the system.

Figure 18:
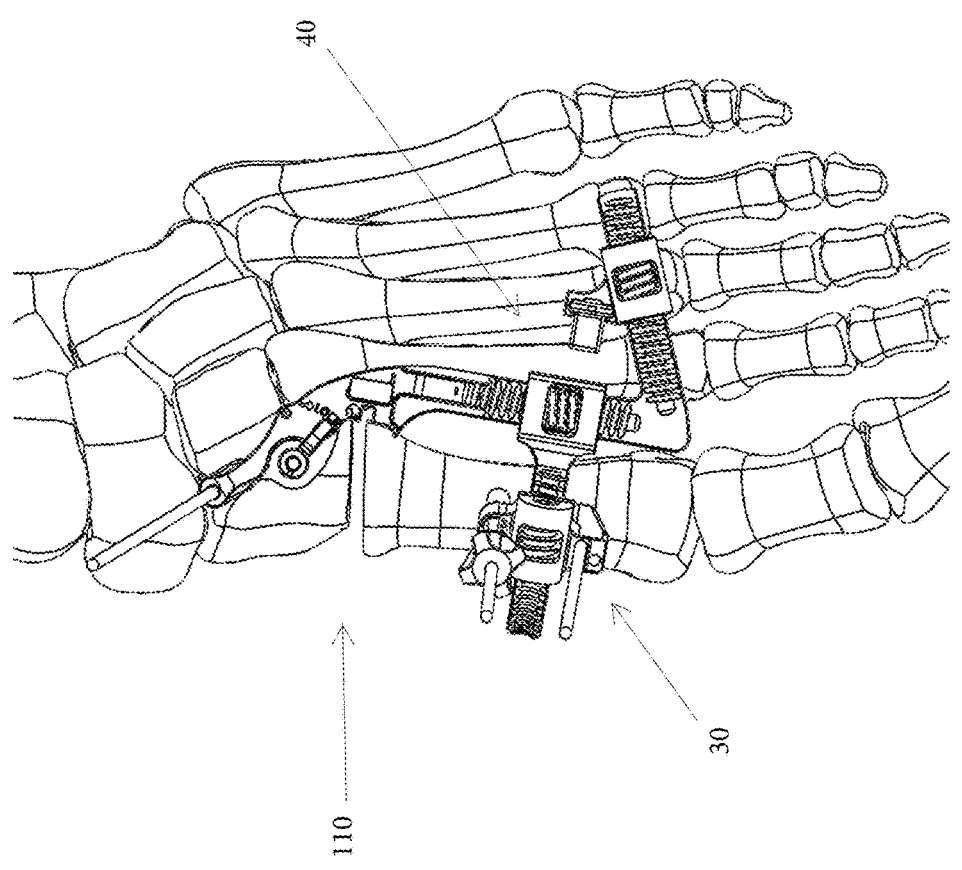
FIG. 18 is a top view of the system of FIG. 16 showing a space between the cuneiform and metatarsal after distraction.

As depicted in FIG. 18, any connected cartridge (e.g., paddle cartridge 50, open saw guide 250, Bur guide cartridge 259) may be removed to reveal a joint space for easy access (for open cutting) to a joint (e.g., joint space 110) between a cuneiform and metatarsal, for example.

Figure 17:
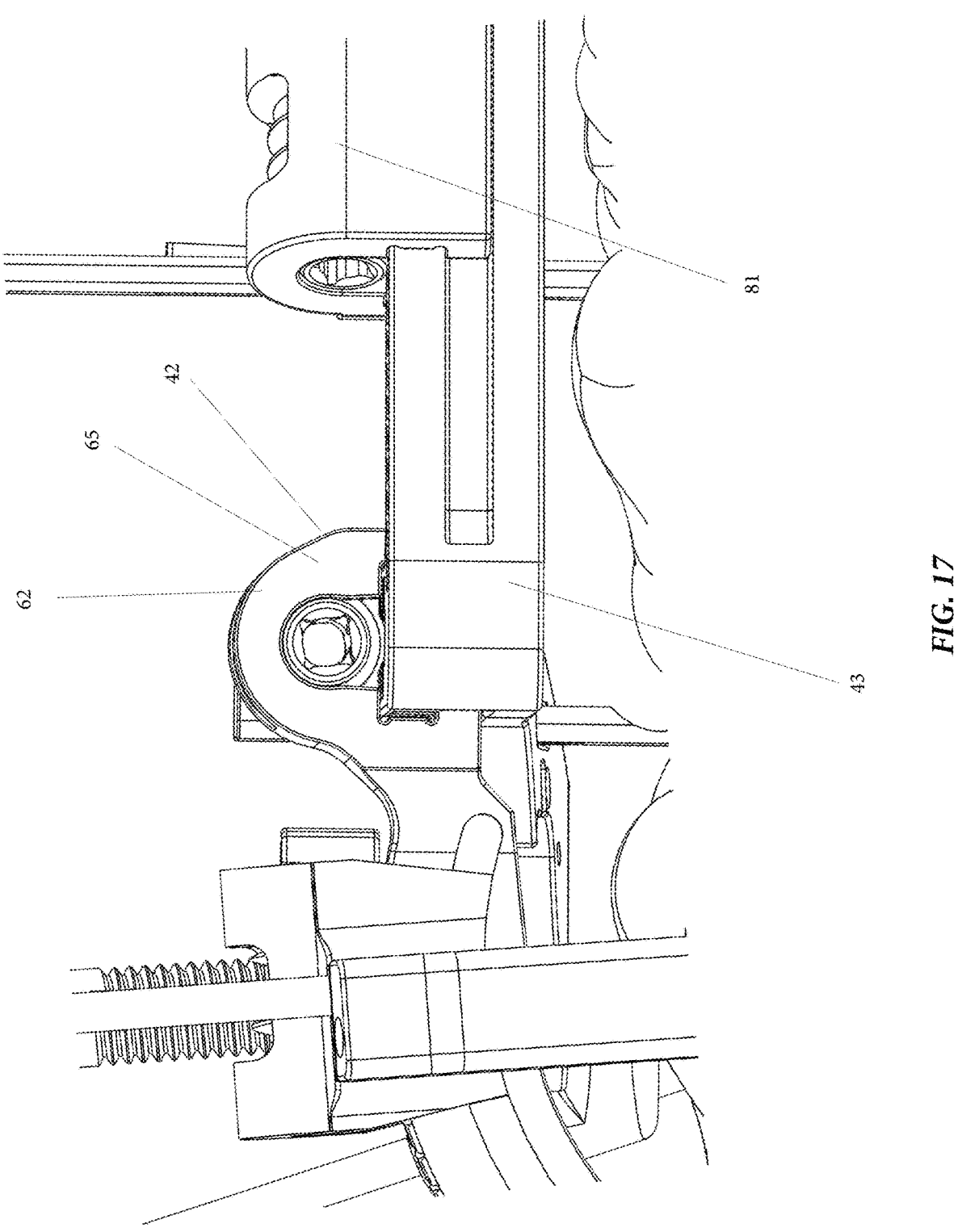
FIG. 17 is a side view of a portion of FIG. 1 showing a drive screw of a compression-distraction mechanism and a drive screw of a lateral extension mechanism.

As depicted in FIG. 17, a driver (e.g., a torx driver) may be inserted into a screwhead or recess 65 of end portion 62 of mobile portion 42 of distraction mechanism 40 to rotate a worm screw 67 received in an interior cavity 47 of mobile portion 42. Worm screw 67 may engage an interior threaded surface (not shown) of mobile portion 42 bounding cavity 47 and a top threaded surface 64 of arm 60. A rotation of the driver and worm screw 67 counter clockwise may cause movement of mobile portion 42 along arm 60 due to the engagement of worm gear 67 with threaded surface 64 and the interior threaded surface of mobile portion 42 to cause a movement of trolley 30 connected to first metatarsal 117 to distract a Tarsometatarsal joint (e.g., joint 110) for final preparation, as depicted.

Figure 19:
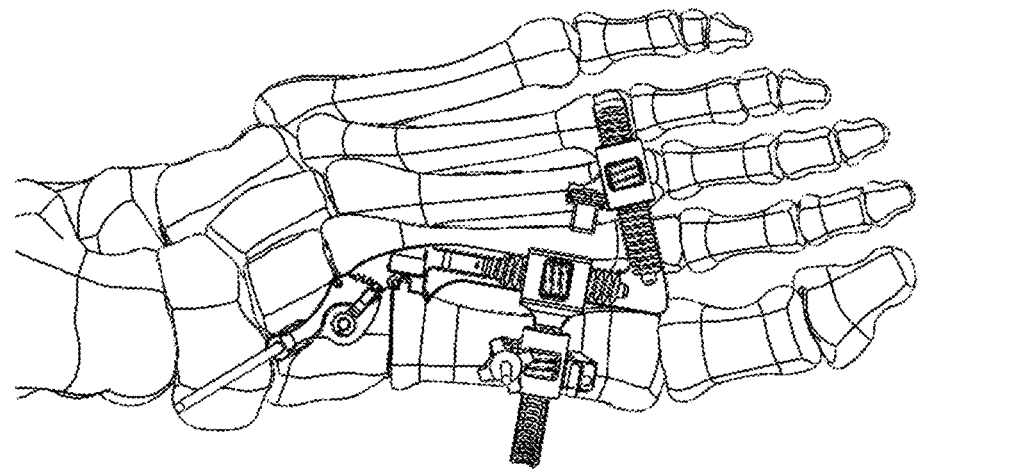
FIG. 19 is a top view of the system of FIG. 18 showing the cuneiform and metatarsal after compression.

After the bones (e.g., proximal cuneiform 115, first metatarsal 117) bounding a joint (e.g., joint 110) have been cut as described above (e.g., using open saw guide 250 and saw 251) or otherwise prepared, the driver may be engaged with worm gear 67 as described above and rotated clockwise, for example, to move mobile portion 42 along arm 60 to move trolley 30 to thereby move a metatarsal (e.g., first metatarsal 117) toward a cuneiform (e.g., proximal cuneiform 115) to compress or close the joint as depicted in FIG. 19.

In an undepicted example, K-wires can be placed across a joint (e.g., joint 110) free handed to keep a first metatarsal (e.g., first metatarsal 117) in place while removing system 10 and an interosseous system may be inserted such as that described in co-owned U.S. patent application Ser. No. 16/293,382 incorporated herein by reference.

As described above, cartridge engaging portion 20 may connect to other tools or functional elements, such as paddle cartridge 50, open saw guide 250, Bur guide cartridge 259 via handle 24, and such elements may also be connected to cartridge engaging portion 20 via other connecting mechanisms in accordance with the described invention in unillustrated examples. Also, other functional elements not described herein desired by a surgeon may be attached to cartridge engaging portion 20 via handle 24 and upwardly projecting portion 25 or other connecting mechanisms.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

We claim:
1. A bone displacement system comprising:
   a mobile portion and an arm, such that the mobile portion is movable along the arm;

a movable trolley positioned laterally relative to the mobile portion, the movable trolley comprising a plantar-dorsal adjustment mechanism configured to engage a first metatarsal and configured to adjust a plantar-dorsal position of the first metatarsal relative to the system; and apertures configured to receive wires to attach the system to bones to accommodate displacement of said first metatarsal.

2. The system of claim 1 further comprising an anchoring portion having an aperture of the apertures for receiving a wire of the wires to connect the anchoring portion to a proximal bone, said anchoring portion connectable to a downwardly depending member for holding a tissue portion.

3. The system of claim 1 wherein said plantar-dorsal adjustment mechanism comprises a threaded member received in a threaded receiving portion of said trolley such that said threaded member is rotatable in said receiving portion to apply the vertical force to the first metatarsal.

4. The system of claim 1 further comprising a lateral body connected to said arm and engageable with a lateral bone.

5. The system of claim 4 wherein said lateral body comprises a lateral extension mechanism having a lateral holding portion connected to a second-downwardly depending portion and movably connected to a rail to allow said lateral holding portion to move laterally relative to a longitudinal axis of said arm.

6. The system of claim 5 wherein said lateral extension mechanism comprises a screw engaging the rail and the lateral holding portion to allow movement of the lateral holding portion and the lateral bone relative to the first metatarsal when a user drives said screw, the trolley is configured to be connected to the first metatarsal, and the downwardly depending member configured to engage the lateral bone.

7. The system of claim 1 further comprising a lateral body connected to the arm, the lateral body comprising a lateral holding portion moveably engaged with a rail and the rail having a rail longitudinal axis, the arm having an arm longitudinal axis, said rail longitudinal axis and said arm longitudinal axis being angled at less than perpendicular to each other.

8. A method for use in bone displacement, comprising:

receiving a wire in an aperture of a bone displacement system to connect the bone displacement system to a bone;

moving a mobile portion along an arm of the system; and engaging a plantar-dorsal adjustment mechanism of a movable trolley with a first metatarsal and adjusting a plantar-dorsal position of the first metatarsal relative to the system, the movable trolley positioned laterally relative to the mobile portion.

9. The method of claim 8 further comprising moving a lateral extension mechanism connected to the arm laterally wherein the lateral extension mechanism comprises a receiving cavity.

10. The method of claim 9 further comprising locating a paddle in the receiving cavity and abutting a side of a second metatarsal with the paddle.

11. The method of claim 8 further connecting a downwardly depending member to an anchoring portion of the bone displacement system and holding a tissue portion away from a joint between a proximal bone and the first metatarsal of the foot by the downwardly depending member.

12. The method of claim 8 wherein the plantar-dorsal adjustment mechanism comprises a threaded member received in a threaded receiving portion of the trolley and wherein the adjusting comprises rotating the threaded member in the receiving portion to apply a vertical force to the first metatarsal to adjust the first metatarsal relative to a proximal bone of the foot.

13. The method of claim 8 further comprising connecting a downwardly depending portion to a lateral body connected to the arm to contact a lateral bone located lateral to the first metarsal.

14. The method of claim 13 wherein the lateral body comprises a lateral extension mechanism having a lateral holding portion connected to the downwardly depending portion and movably connected to a rail to allow the lateral holding portion to move laterally relative to a longitudinal axis of a compression-distraction mechanism connected to the trolley.

15. The method of claim 14 further comprising driving a screw engaging the rail to move the lateral holding portion to move the downwardly depending portion to move the lateral bone relative to the first metatarsal.

16. The method of claim 14 further comprising extending a second wire through a second aperture of the plantar-dorsal adjustment mechanism to connect the trolley to the first metatarsal.

* * * * *